US010401318B2

(12) United States Patent
Rigas

(10) Patent No.: US 10,401,318 B2
(45) Date of Patent: Sep. 3, 2019

(54) BREATH ANALYZER AND BREATH TEST METHODS

(71) Applicant: Anastasia Rigas, Setauket, NY (US)

(72) Inventor: Anastasia Rigas, Setauket, NY (US)

( * ) Notice: Subject to any disclaimer, the term of this patent is extended or adjusted under 35 U.S.C. 154(b) by 246 days.

(21) Appl. No.: 15/312,877

(22) PCT Filed: May 22, 2015

(86) PCT No.: PCT/US2015/032156
§ 371 (c)(1),
(2) Date: Nov. 21, 2016

(87) PCT Pub. No.: WO2015/179751
PCT Pub. Date: Nov. 26, 2015

(65) Prior Publication Data
US 2017/0191953 A1  Jul. 6, 2017

Related U.S. Application Data

(63) Continuation-in-part of application No. 13/420,321, filed on Mar. 14, 2012, now Pat. No. 9,678,058.

(60) Provisional application No. 62/013,133, filed on Jun. 17, 2014, provisional application No. 62/001,832, filed on May 22, 2014, provisional application No. 61/452,507, filed on Mar. 14, 2011.

(51) Int. Cl.
| | | |
|---|---|---|
| A61B 5/08 | (2006.01) |
| G01N 27/12 | (2006.01) |
| G01N 33/497 | (2006.01) |
| A61B 5/097 | (2006.01) |
| A61B 5/00 | (2006.01) |
| G01N 33/84 | (2006.01) |

(52) U.S. Cl.
CPC ........... *G01N 27/126* (2013.01); *A61B 5/082* (2013.01); *A61B 5/097* (2013.01); *A61B 5/42* (2013.01); *G01N 33/497* (2013.01); *G01N 33/84* (2013.01); *A61B 5/4255* (2013.01); *A61B 2560/0431* (2013.01); *A61B 2560/0443* (2013.01); *G01N 2033/4975* (2013.01); *G01N 2800/06* (2013.01)

(58) Field of Classification Search
CPC combination set(s) only.
See application file for complete search history.

(56) References Cited

U.S. PATENT DOCUMENTS

| | | | |
|---|---|---|---|
| 3,852,036 A | 12/1974 | Burroughs et al. |
| 3,953,173 A | 4/1976 | Obayashi et al. |
| (Continued) | | |

FOREIGN PATENT DOCUMENTS

| | | |
|---|---|---|
| DE | 29902593 U1 | 8/1999 |
| EP | 2203563 A1 | 7/2010 |
| (Continued) | | |

OTHER PUBLICATIONS

European Patent Application No. 15795334.0, Extended European Search Report dated Dec. 21, 2017, 8 pages.
(Continued)

*Primary Examiner* — Navin Natnithithadha
*Assistant Examiner* — Eric J Messersmith
(74) *Attorney, Agent, or Firm* — Fredrikson & Byron, P.A.

(57) ABSTRACT

The present invention provides an improved breath analyzer and breath test method to determine the presence of a gastrointestinal disorder in a subject's digestive tract.

20 Claims, 7 Drawing Sheets

(56) References Cited

U.S. PATENT DOCUMENTS

| | | | |
|---|---|---|---|
| 4,007,063 A | 2/1977 | Yasuda et al. |
| 4,030,340 A | 6/1977 | Chang |
| 4,140,106 A | 2/1979 | Kirmaier |
| 4,169,369 A | 10/1979 | Chang |
| 4,346,583 A | 8/1982 | Hoogstraat |
| 4,430,191 A | 2/1984 | Sone et al. |
| 4,481,499 A | 11/1984 | Arima et al. |
| 4,753,916 A | 6/1988 | Carcia et al. |
| 4,823,803 A | 4/1989 | Nakamura |
| 4,895,705 A | 1/1990 | Wrighton et al. |
| 4,947,861 A | 8/1990 | Hamilton et al. |
| 5,037,525 A | 8/1991 | Badwal et al. |
| 5,055,441 A | 10/1991 | McCarron et al. |
| 5,069,220 A | 12/1991 | Casparie et al. |
| 5,252,292 A | 10/1993 | Hirata et al. |
| 5,531,225 A | 7/1996 | Nawata et al. |
| 5,546,004 A | 8/1996 | Schmelz et al. |
| 5,624,640 A | 4/1997 | Potthast et al. |
| 5,783,154 A | 7/1998 | Althainz et al. |
| 5,787,885 A | 8/1998 | Lemelson et al. |
| 5,811,662 A | 9/1998 | Williams et al. |
| 5,858,186 A | 1/1999 | Glass et al. |
| 5,869,007 A | 2/1999 | Jang |
| 5,969,231 A | 10/1999 | Qu et al. |
| 5,993,625 A | 11/1999 | Inoue et al. |
| 6,156,346 A | 12/2000 | Chen et al. |
| 6,173,602 B1 | 1/2001 | Moseley |
| 6,173,603 B1 | 1/2001 | Horn |
| 6,186,958 B1 | 2/2001 | Katzman et al. |
| 6,234,006 B1 | 5/2001 | Sunshine et al. |
| 6,319,724 B1 | 11/2001 | Lewis et al. |
| 6,411,905 B1 | 6/2002 | Guoliang et al. |
| 6,467,333 B2 | 10/2002 | Lewis et al. |
| 6,491,643 B2 | 12/2002 | Katzman et al. |
| 6,606,566 B1 | 8/2003 | Sunshine |
| 6,609,068 B2 | 8/2003 | Cranley et al. |
| 6,620,109 B2 | 9/2003 | Hanson, III |
| 6,660,231 B2 | 12/2003 | Moseley |
| 6,703,241 B1 | 3/2004 | Sunshine et al. |
| 6,723,056 B1 | 4/2004 | Alving et al. |
| 6,767,732 B2 | 7/2004 | Alocilja et al. |
| 6,820,012 B2 | 11/2004 | Sunshine |
| 6,839,636 B1 | 1/2005 | Sunshine et al. |
| 6,841,391 B2 | 1/2005 | Lewis et al. |
| 6,981,947 B2 | 1/2006 | Melker |
| 7,014,612 B2 | 3/2006 | Hubbard et al. |
| 7,017,389 B2 | 3/2006 | Gouma |
| 7,101,340 B1 | 9/2006 | Braun |
| 7,104,963 B2 | 9/2006 | Melker et al. |
| 7,220,387 B2 | 5/2007 | Flaherty et al. |
| 7,338,454 B2 | 3/2008 | Butler et al. |
| 7,364,551 B2 * | 4/2008 | Allen .................. A61B 5/411 |
| | | | 600/531 |
| 7,522,040 B2 | 4/2009 | Passmore et al. |
| 7,640,789 B2 | 1/2010 | Kim et al. |
| 7,687,275 B2 | 3/2010 | Burdinski |
| 7,704,214 B2 | 4/2010 | Abraham-Fuchs et al. |
| 7,867,171 B2 | 1/2011 | Ben-Oren et al. |
| 7,950,271 B2 | 5/2011 | Novak et al. |
| 7,981,215 B2 | 7/2011 | Gouma et al. |
| 8,263,002 B1 | 9/2012 | Chow et al. |
| 8,343,484 B2 | 1/2013 | Farmer et al. |
| 8,485,983 B2 | 7/2013 | Gouma et al. |
| 9,289,155 B2 | 3/2016 | Rigas et al. |
| 9,541,517 B2 | 1/2017 | Samuilov |
| 2002/0011569 A1 | 1/2002 | Mori et al. |
| 2002/0159950 A1 | 10/2002 | Wagner |
| 2003/0008407 A1 | 1/2003 | Fu |
| 2003/0105407 A1 | 6/2003 | Pearce, Jr. et al. |
| 2003/0175699 A1 | 9/2003 | Tachikawa et al. |
| 2003/0208133 A1 | 11/2003 | Mault |
| 2003/0217586 A1 | 11/2003 | Gouma |
| 2004/0077965 A1 | 4/2004 | Hubbard et al. |
| 2005/0100535 A1 | 5/2005 | Farmer et al. |
| 2005/0129573 A1 | 6/2005 | Gabriel et al. |
| 2005/0171449 A1 | 8/2005 | Suslick et al. |
| 2006/0074335 A1 | 4/2006 | Ben-Oren et al. |
| 2006/0147496 A1 | 7/2006 | Lin et al. |
| 2006/0174385 A1 | 8/2006 | Gruber et al. |
| 2006/0277974 A1 | 12/2006 | Gouma et al. |
| 2007/0048181 A1 | 3/2007 | Chang et al. |
| 2007/0167691 A1 | 7/2007 | Causevic |
| 2007/0209937 A1 | 9/2007 | Hoagland et al. |
| 2007/0256477 A1 | 11/2007 | Moor |
| 2007/0272901 A1 | 11/2007 | Gouma |
| 2008/0053194 A1 | 3/2008 | Ahmad |
| 2008/0077037 A1 | 3/2008 | Gouma et al. |
| 2008/0093226 A1 | 4/2008 | Briman et al. |
| 2008/0317636 A1 | 12/2008 | Brahim et al. |
| 2009/0031784 A1 | 2/2009 | Koda et al. |
| 2009/0187111 A1 | 7/2009 | Reilly, Jr. et al. |
| 2009/0266411 A1 | 10/2009 | Habib et al. |
| 2009/0294303 A1 | 12/2009 | Fischer et al. |
| 2010/0012919 A1 | 1/2010 | Park et al. |
| 2010/0089772 A1 | 4/2010 | Deshusses et al. |
| 2010/0209507 A1 | 8/2010 | Lin et al. |
| 2010/0212403 A1 | 8/2010 | Seal et al. |
| 2010/0215738 A1 | 8/2010 | Ritter et al. |
| 2011/0056846 A1 | 3/2011 | Neethirajan et al. |
| 2011/0061446 A1 | 3/2011 | Gouma et al. |
| 2011/0259083 A1 | 10/2011 | Lee et al. |
| 2012/0034646 A1 | 2/2012 | Rigas et al. |
| 2012/0065534 A1 | 3/2012 | Rigas |
| 2012/0186999 A1 | 7/2012 | Walton et al. |
| 2012/0234076 A1 * | 9/2012 | Rigas .................. G01N 33/497 |
| | | | 73/23.3 |
| 2012/0237968 A1 | 9/2012 | Rigas |
| 2014/0221863 A1 | 8/2014 | Rigas |
| 2014/0330153 A1 | 11/2014 | Gouma et al. |
| 2015/0250407 A1 | 9/2015 | Rigas |
| 2016/0097761 A1 | 4/2016 | Sano et al. |
| 2016/0103082 A1 | 4/2016 | Kimura |
| 2017/0105656 A1 | 4/2017 | Rigas |

FOREIGN PATENT DOCUMENTS

| | | |
|---|---|---|
| EP | 2685891 A2 | 1/2014 |
| KR | 101314303 B1 | 10/2013 |
| WO | 0193915 A1 | 12/2001 |
| WO | 0206822 A1 | 1/2002 |
| WO | 03041565 A2 | 5/2003 |
| WO | 2009039152 A1 | 3/2009 |
| WO | 2011004567 A1 | 1/2011 |
| WO | 2012125734 A2 | 9/2012 |
| WO | 2012125745 A2 | 9/2012 |
| WO | 2014056961 A1 | 4/2014 |
| WO | 2014063169 A1 | 4/2014 |
| WO | 2015179751 A1 | 11/2015 |
| WO | 2015179755 A1 | 11/2015 |

OTHER PUBLICATIONS

European Patent Application No. 15796893.4, Partial Supplementary European Search Report dated Dec. 20, 2017, 15 pages.

Sadek et al., "A Room Temperature Polyaniline Nanofiber Hydrogen Gas Sensor," Sensor Technology Laboratory, RMIT University, 2005 IEEE, pp. 207-210.

Abdel-Saheb, Ibrahim, Memorandum: Review of Urea, as an Active and Inert Ingredient Environmental Protection Agency, (2001) Retrieved from Internet on Apr. 1, 2016 at <URL: http://web.archive.org/web/20040722194412/http://www.epa.gov/oppsrrd1/reregistration/urea/UreaEnviron.pdf> 14 pages.

Agha et al., "Evidence-based examination of the African enigma in relation to Helicobacter pylori infection," Scandinavian Journal of Gastroenterology (2005) 40:523-529, Taylor & Francis Group Ltd, United Kingdom.

ALCOSCAN™ Al2000 Alcohol Breath Analyzer, Craig Medical Distribution Inc., 3 pages, retrieved from Internet on Mar. 29, 3026 at <URL: http://www.craigmedical.com/alcoscan_AL_2000.htm.

Brandli, 0. et al., Lung function in healthy never smoking adults: reference values and lower limits of normal of a Swiss population.

(56) References Cited

OTHER PUBLICATIONS

Thorax (1996) 51:277-283. Retrieved from the Internet on Mar. 19, 2016 at < http://thorax.bmj.com/>.
Brown, L. M. Helicobacter pylori: epidemiology and routes of transmission. Epidemiol Rev (2000) 22:283-297.
Casellas et al., "Hydrogen Breath Test with D-Xylose for Celiac Disease Screening is as Useful in the Elderly as in Other Age Groups," Digestive Diseases and Sciences, Oct. 2001, vol. 46, No. 10, pp. 2201-2205.
Chen, Jyh-Cherng et al., Removal of carbon dioxide by a spray dryer, Chemosphere, (2005) 59:99-105, <doi:10.1016/i.chemosphere.2004.09.076>.
Chung, Yong-Keun et al., Gas sensing properties of WO3 thick film for NO2 gas dependent on process condition, Sensors and Actuators B: Chemical (1999) 60:49-56 <doi:10.1016/S0925-4005(99)00243-9>.
Corazza et al., "Fast Breath Hydrogen in Celiac Disease," Pub Med, Gastroenterology, vol. 93, No. 1, Jul. 1987; pp. 53-58.
Cutler, Alan F., Testing for Helicobacter pylori in clinical practice. Symposium on Helicobacter Pylori, Am J Med (1996) 100:35S-41S, Supplement 5 [Discussion pp. 39S-41S].
Cutler, Alan F. et al., Accuracy of invasive and noninvasive tests to diagnose Helicobacter pylori infection, Gastroenterology (1995) 109:136-141, American Gastroenterological Association.
Dai, Liming, et al., Sensors and sensor arrays based on conjugated polymers and carbon nanotubes; Pure App. Chem., vol. 74, No. 9, pp. 1753-1772, 2002.
Decarbite®, P.W. Perkins Co., Inc., Safety Data Sheet (Jan. 5, 2015) 4 pages.
Delaney, B., et al., Review article: Helicobacter pylori and gastroesophageal reflux disease. Aliment Pharmscol Ther (2005) 22 Suppl 1 :32-40.
Di Francesco, F., et al., Breath analysis: trends in techniques and clinical applications. Microchemical Journal (2005) 79:105-410.
Dunn, B.E. et al., Helicobacter pylori. Clinical Microbiology Reviews (1997) pp. 720-741, vol. 10, Issue 4, retrieved from the Internet on Mar. 19, 2016 at <URL: http://cmr.asm.org/>.
Dutta, Prabir, et al., Interaction of Carbon Monoxide with Anatase Surfaces at High Temperatures: Optimization of a Carbon Monoxide Sensor, J. Phys. Chem. B., 103, pp. 4412-4419, (1999).
Dutta, Ritaban et al., Classification of Ear, Nose and Throat Bacteria Using a Neural-Network-Based Electronic Nose; Mrs Bulletin, Oct. 2004, pp. 709-713, Materials Research Society http://www.mrs.org/publications/.
Eshun, J.K. et al., Comparison of immunohistochemistry and silver stain for the diagnosis of pediatric Helicobacter pylori infection in urease-negative gastric biopsies. Pediatr Dev Patho (2001) 4:82-88.
Eslick, G.D. et al., Association of Helicobacter pylori infection with gastric carcinoma: a meta-analysis. Am J Gastroenterol (1999) 94:(9) 2373-2379.
European Pat. App. No. 08832402.5, Extended European Search Report dated Jun. 20, 2013, 8 pages.
European Pat. App. No. 12757976.1, Extended European Search Report dated Feb. 18, 2015, 9 pages.
Ferroni, A. et al., Nanosized thin films of tungsten-titanium mixed oxides as gas sensors, Sensors and Actuators B 58 (1999) pp. 289-294.
Gatta, L. et al., A rapid, low-dose, 13C-urea tablet for the detection of Helicobacter pylori infection before and after treatment. Aliment Pharmacal Ther (2003) 17:793-798.
Giner Electrochemical (trace) Gas Sensors. Datasheet [online]. Giner, In.c, retrieved from the Internet on Apr. 22, 2016 at <URL: http://www.ginerinc.com/products.php?a=TGSI>.
Gisbert, J.P. et al., Accuracy of Helicobacter pylori Diagnostic Tests in Patients with Bleeding Peptic Ulcer: A Systematic Review and Meta-analysis. Am J Gastroenterol (2006) 101:848-863.
Gisbert, J.P. et al., Review article: 13C-urea breath test in the diagnosis of Helicobacter pylori infection—a critical review. Aliment Pharmacal Ther (2004) 20:1001-1017.
Gisbert, J.P., The recurrence of Helicobacter pylori infection: incidence and variables influencing it. A critical review. Am J Gastroenterol (2005) 100:2083-2099.
Go, M.F. Review article: natural history and epidemiology of Helicobacter pylori infection. Aliment Pharmacol Ther 16 Suppl (2002) 1:3-15.
Gouma, P. et al., Novel Materials and Applications of Electronic Noses and Tongues; MRS. Bulletin, Oct. 2004, pp. 697-702.
Gouma, P.I. et al., Microstructural Characterization of Sensors based on Electronic Ceramic Materials, JOM, 50 (11), presented as JOM-e., Nov. 1998, 15 pages.
Gouma, P.I. et al., Selective nanoprobes for 'signalling gases', Nanotechnology 17 (2006) S48-S53, retrieved from the Internet on Mar. 19, 2016 at <URL: http://iopscience.iop.org/article/10.1088/0957-4484/17/4/008/meta; isessionid=DEE5CDBA0DD81DDF45C9D0CA79F53344.c3>.
Gouma, P.I. et al., Structural Stability of Titania Thin Films, Nanostructured Materials (1999) 11(8), pp. 1231-1237.
Gouma, et al., TiO2-based Gas Sensors as Thick or Thin Films: An Evaluation of the Microstructure. Proceedings of the International Symposium on Dielectric Ceramics, May 2-6, 1998 and Ceramic Transactions: Dielectric Ceramic Materials, (1999) vol. 100, pp. 419-428, The American Ceramic Society, Westerville, Ohio.
Gouma, Pelagia I. et al., Fabrication of Free-Standing Titania-Based Gas Sensors by the Oxidation of Metallic Titanium Foils. J. Am Ceramic. Soc., 83(4), pp. 1007-1009, 2000.
Graham, D.Y ., et al., Challenge model for Helicobacter pylori infection in human volunteers. Gut (2004) 53:1235-1243, retrieved the Internet on Mar. 19, 2016 at <URL: http://gut.bmj.com/>. Published by group.bmj.com.
Guidi, V. et al., Nanosized Ti-doped Mo03 thin films for gas-sensing application. Sens and Act B, (2001) 77:555-560.
Harris, Adam et al., Treating Helicobacter pylori—the best is yet to come? Gut (1996) 39:781-783, retrieved from the Internet on Mar. 19, 2016 at <URL: http://gut.bmj.com/>. Published by group.bmj.com.
He, Lifang et al., Gas Sensors for ammonia detection based on polyaniline-coated multi-wall carbon nanotubes (2009) Materials Science and Engineering B, 163:76-81.
Helmus, Michael N., et al., Nanotechnology-enabled chemical sensors and biosensors. American Laboratory (2006) 38:34-38.
Hryniuk, Alexa et al., A Preliminary Investigation of Exhaled Breath from Patients with Celiac Disease Using Selected Ion Flow Tube Mass Spectrometry. J Gastrointestin Liver Dis. (2010) 19(1) pp. 15-20, Lakehead University , Thunder Bay, Ontario, Canada.
Hu, Li Tai et al., Purification and N-terminal analysis of urease from Helicobacter pylori. Infect Immun (1990) 58:992-998.
Humerfelt, S., et al., Forced expiratory volume in 1 second (FEV1) and forced vital capacity (FVC) variability in asymptomatic neversmoking men. Clin Physio. (1998) 18:387-396.
Hunt, R.H., Peptic Ulcer Disease: Defining the Treatment Strategies in the Era of Helicobacter pylori. Am J Gastroentero. (1997) 92:36S-40S; discussion 40S-43S.
Imawan, C.et al., A new preparation method for sputtered MoO3 multilayers for the application in gas layers, Sensors and Actuators B. 78 (2001) pp. 119-125.
Imawan, C., et al., Gas-sensing characteristics of modified-MoO2 thin films using Ti-overlayers for NH3 gas sensors, Sensors and Actuators B. 64 (2000) pp. 193-197.
International Pat. App. No. PCT/US2015/032162, International Search Report and Written Opinion dated Oct. 16, 2015, 16 pages.
International Pat. App. No. PCT/US2012/029103, International Search Report dated Jun. 13, 2012, 3 pages.
International Pat. App. No. PCT/US2012/029087, International Preliminary Report on Patentability dated Feb. 4, 2014, 6 pages.
International Pat. App. No. PCT/US2012/029087, International Search Report and Written Opinion dated Jul. 6, 2012, 5 pages.
Biesiekierski Jr, et al., "No Effects of Gluten in Patients With Self-Reported Non-Celiac Gluten Sensitivity After Dietary Reduction of Fermentable, Poorly Absorbed, Short-Chain Carbohydrates," Gastroenterology, vol. 145, Aug. 2013, pp. 320-328.

(56) References Cited

OTHER PUBLICATIONS

International Patent Application No. PCT/US2015/032156, International Search Report and Written Opinion dated Aug. 26, 2015, 13 pages.
Kato, Seiichi et al., Diagnostic Accuracy of the 13C-Urea Breath Test for Childhood Helicobacter pylori Infection: A Multicenter Japanese Study the American J of Gastroenterology, (2002) 97(7):1668-1673.
Kearney, David J. et al., Breath Ammonia Measurement in Helicobacter pylori Infection, Dig Dis Sci (2002) 47:2523-2530.
Kharitonov, Sergei A. et al., Exhaled markers of pulmonary disease. Am J Respir Crit Care Med (2001) 163:1693-1722.
Klein, Peter O. et al., Noninvasive detection of Helicobacter pylori infection in clinical practice: the 13C urea breath test. Am J Gastroentero. (1996) 91:690-694.
Leong, R.W. et al., Review article: Helicobacter species and hepatobiliary diseases. Aliment Pharmacal Ther (2002) 16:1037-1045.
Leung, Wai K. Helicobacter pylori and Gastric Neoplasia. Contrib Microbio (2006) 13:66-80.
Livage, Jacques et al., Encapsulation of biomolecules in silica gels. J. Phys.: Condens. Matter 13 (2001) pp. R673-R691, retrieved from the Internet on Mar. 20, 2016 at <URL: http://iopscience.iop.org/.
Lupan et al., "Selective hydrogen gas nanosensor using individual ZnO nanowire with fast response at room temperature," Sensors and Actuators B vol. 144, 2010, pp. 56-66.
Marquis, Brent T. et al., A semiconducting metal oxide sensor array for the detection of NOx and NH3, Sensors and Actuators B 77 (2001) pp. 100-110.
Minoli, Giorgio et al., A Simplified Urea Breath Test for the Diagnosis of Helicobacter pylori Infection Using the LARA System. Laser Assisted Ratio Analyzer. J Clin Gastroenterol. (1998) 26:264-266; retrieved from the Internet on Mar. 28, 2016 at <URL: http://journals.lww.com/jcge/Abstract/1998/06000/A_Simplified_Urea_Breath_Test_for_the_Diagnosis_of.9.aspx>.
Monteiro, Lurdes et al., Evaluation of performances of three DNA enzyme immunoassays for detection of Helicobacter pylori PCR products from biopsy specimens. J Clin Microbiol. (1997) 35:2931-2936.
Murakami, Kazunari et al., Latest insights into the effects of Helicobacter pylori infection on gastric carcinogenesis. World J Gastroentero. (2006) 12:2713-2720.
Murnick, D.E. et al., Laser-Based Analysis of Carbon Isotope Ratios. Science (1994) 263:945-947, retrieved from the Internet on Mar. 22, 2016 at <URL: http://science.sciencemag.org/content/263/5149/945.full-text.pdf+html>.
Mutschall, D., et al., Sputtered molybdenum oxide thin films for NH3 detection 1996 Sensor and Actuators B35-36, p. 320-324.
*Nanomedicon, LLC v. Research Found. of State Univ. of N.Y.*, 2012 NY slip Op 33742(U), Mar. 15, 2012, Supreme Court, Suffolk County, Docket No. 36815-2010, Judge: Emily Pines, 14 pages.
O'Morain, Colm. Role of Helicobacter pylori in functional dyspepsia. World J Gastroentero. (2006) 12:2677-2680.
Otsuka America Inc., BreathTek Urea Breath Test, retrieved from the Internet on Mar. 31, 2016 at <http://web.archive.org/web/20120228152952/http://www.otsuka-us.com/Products/Pages/BreathTek.aspx>, 2 pages.
Papatheodoridis, George V. et al., Effects of Helicobacter pylori and nonsteroidal anti-inflammatory drugs on peptic ulcer disease: a systematic review. Clin Gastroenterol Hepato. (2006) 4:130-142.
Pardo, Matteo et al., Electronic Olfactory Systems Based on Metal Oxide Semiconductor Sensor Arrays. MRS Bulletin, Oct. 2004, pp. 703-708, Materials Research Society http://www.mrs.org/publications/.
Penner, J.L. et al., Serotyping of Campylobacter jejuni and *Campylobacter coli* on the Basis of Thermostable Antigens. Eur J Clin Microbial. (1983) 2:378-383.

Phillips, Michael, Detection of volatile organic compounds in breath. In "Disease markers in exhaled breath" eds Marczin N. Kharitonov SA, Yacoub MH and Barnes PJ. Marcel Decker. (2002) pp. 219-231, New York.
Prasad, A.K. et al., Comparison of sol-gel and ion beam deposited MoO3 thin film gas sensors for selective ammonia detection. Sens Actuators B. (2003) 93:25-30.
Prasad, A.K., et al., Reactivity sputtered Mo03 films for ammonia sensing. Thin Solid Films (2003) 436:46-51.
Quest Diagnositics, Helicobacter pylori Urea Breath Test (UBiT), retrieved from the Internet on Mar. 20, 2016 at <URL: http://www.questdiagnostics.com/hcp/topics/gastroent/hpylori_breath.html> 3 pages.
Rana et al., "Influence of Previously Ingested Wheat on Fasting Breath Hydrogen in Celiac Patients," Dig. Dis. Sci., vol. 54, No. 6, 2009, pp. 1276-1279.
Romagnuolo, Joseph et al., Using Breath Tests Wisely in a Gastroenterology Practice: An Evidence-Based Review. Am J Gastroentero. (2002) 97: 1113-1126.
Ryan, M.A. et al., Polymer-Carbon Black Composite Sensors in an Electronic Nose for Air-Quality Monitoring; MRS Bulletin, Oct. 2004, pp. 714-719.
Sberveglieri, G. et al., WO3 sputtered thin films for NOx monitoring, Sensors and Actuators B 26 (1995) pp. 89-92.
Slomianski, Arie et al., [13C]urea breath test to confirm eradication of Helicobacter pylori. Am J Gastroentero. (1995) 90:224-226.
Sonnenberg, Amnon et al., The prevalence of Self-Reported Peptic Ulcer in the United States. Am J Public Health (1996) 86:200-205.
Stejskal, J., Polyaniline. Preparation of a Conducting Polymer (IUPAC Technical Report). Pure Appl. Chem., (2002) vol. 74, No. 5, pp. 857-867, International Union of Pure and Applied Chemistry.
Surveyor, Ivor et al., The 14C-urea breath-test for the detection of gastric Campylobacter pylori infection. Med J Aust (1989) 151:435-439.
Suslick, Kenneth S., An Optoelectronic Nose: "Seeing" Smells by Means of Colorimetric Sensor Arrays; MRS Bulletin, Oct. 2004, pp. 720-725, Materials Research Society http://www.mrs.org/publications/.
Timmer, Bjorn et al., Ammonia sensors and their applications—a review. Sensors and Actuators B, 2005, 107:666-677.
Tveito, Kari et al., 13C-xylose and 14C-xylose breath tests for the diagnosis of coeliac disease. Scandinavian J. Gastroenterol 2008; 43(2): 166-763. SUNY State University of New York, Stony Brook. Taylor & Francis Ltd.
Tveito, Kari et al., A novel one-hour 13C-sorbitol breath test versus the H2-sorbitol breath test for assessment of coeliac disease. Scandinavian J. Gastroenterol (2009) 44(7): 813-9. SUNY State University of New York, Stony Brook. Taylor & Francis Ltd.
Vaira, Dino et al., Peptic ulcer and Helicobacter pylori: update on testing and treatment. Postgrad Med (2005) 117:17-22, 46. Retrieved from the Internet on Mar. 22, 2016 at <URL: http://dx.doi.org/10.3810/pgm.2005.06.1654> Taylor & Francis Ltd.
Versalovic, James, Helicobacter pylori. Pathology and diagnostic strategies. Am J Clin Patho (2003) 119:403-412. Retrieved from the Internet on Mar. 22, 2016 at <URL: http://ajcp.oxfordjournals.org>.
Wang, Xiaodong et al., An integrated array of multiple thin-film metal oxide sensors for quantification of individual components in organic vapor mixtures, Sensors and Actuators B, (1993) 13-14, 458-461.
Weir, Susan, et al., Recurrent Bacteremia Caused by a "Flexispira"-Like Organism in a Patient with X-Linked (Bruton's) Agammaglobulinemia. J Clin Microbio (1999) 37:2439-2445. Retrieved from the Internet on Mar. 28, 2016 at <URL: http://jcm.asm.org>.
Winquist, F. et al., Electronic Tongues. MRS Bulletin, Oct. 2004, pp. 726-731, Materials Research Society http://www.mrs.org/publications/.
Xu, C.N. et al., Selective detection of NH over NO in combustion exhausts by using Au and MoO3 doubly promoted WO element Sensors and Actuators B, (2000) 65, pp. 163-165.
European Patent Application No. 15796893.4, Extended European Search Report dated Aug. 22, 2018, 13 pages.

\* cited by examiner

Figure 4
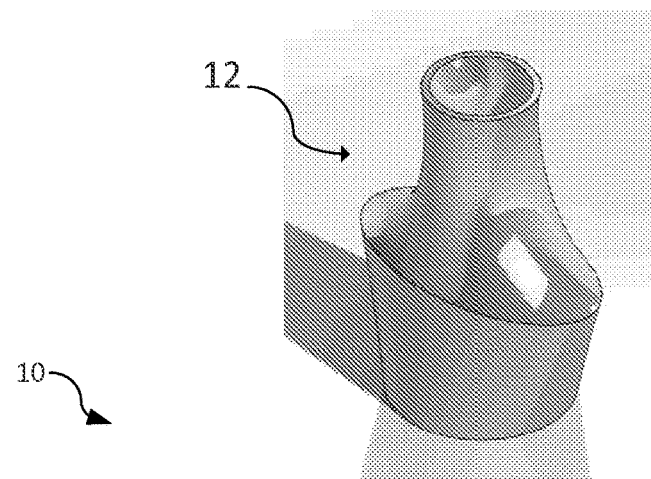
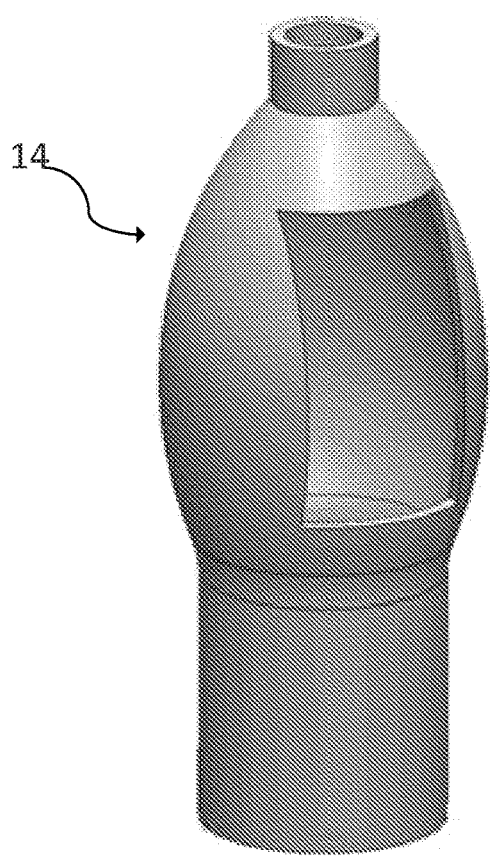

BREATH ANALYZER AND BREATH TEST METHODS

PRIORITY

This application is a 35 U.S.C. 371 national stage filing from International Application No. PCT/US2015/032156, filed May 22, 2015, which claims priority to U.S. provisional application Nos. 62/001,832 and 62/013,133 and is also a continuation-in-part of U.S. utility application Ser. No. 13/420,321, which claims priority to U.S. provisional application Nos. 61/452,507 and 61/452,391, each of which are herein incorporated by reference.

FIELD

The present application relates generally to a breath analyzer and a breath test method for detecting hydrogen in breath to determine presence of a gastrointestinal disorder in a subject's digestive tract.

BACKGROUND

Gastrointestinal disorders are known. Celiac disease is an immune mediated enteropathy caused by ingestion of gluten, a protein found in wheat, and affects people who are genetically predisposed. Non-celiac gluten sensitivity (NCGS) is caused by the ingestion of gluten as well. Lactose intolerance is caused because of inability to digest lactose, a carbohydrate contained in dairy products, due to lack or decreased production of the enzyme lactase by the intestine. Fructose intolerance is caused by the inability to digest fructose, a carbohydrate found in fruits, due to lack or decreased production of the enzyme aldolase B by the intestine. Small intestinal bacterial overgrowth (SIBO) is caused by abnormally increased number of bacteria in the small bowel.

Current methods for diagnosing these gastrointestinal disorders have drawbacks. It would be desirable to provide easy, non-invasive and reliable point-of-care device and test to determine presence of celiac disease, NCGS, lactose intolerance, fructose intolerance and/or SIBO. It would also be desirable to provide a device and test that is less costly, less cumbersome and more convenient than existing tests.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

FIG. 4 shows an embodiment of a breath analyzer with a removable mouthpiece and a main body in a detached configuration;

SUMMARY

Figure 1:
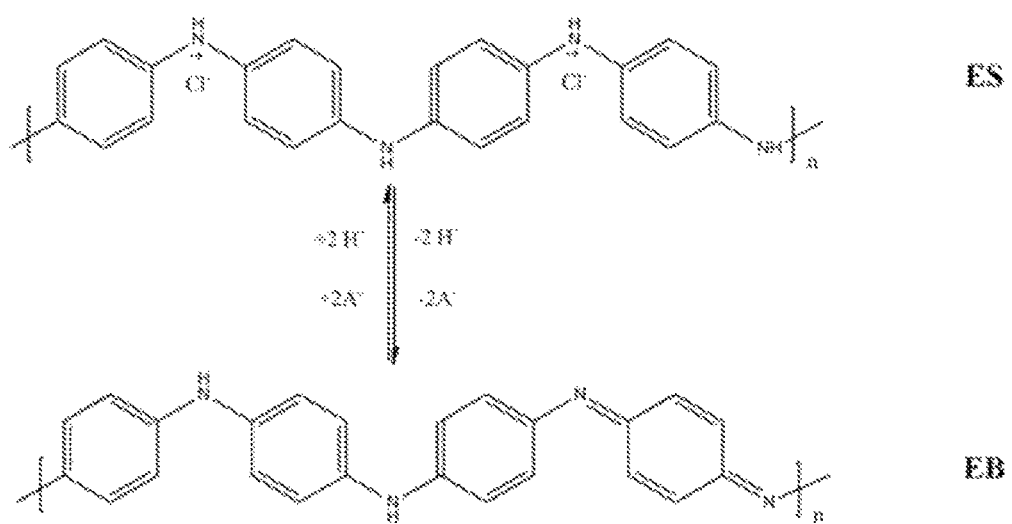
FIG. 1 illustrates an acid-base (emeraldine salt (ES)-emeraldine base (EB)) transition for polyaniline.

The present invention provides a breath analyzer and breath test method to determine the presence of hydrogen in a subject's digestive tract. Subjects afflicted either by celiac disease, non-celiac gluten sensitivity, lactose intolerance, fructose intolerance or small bowel bacterial overgrowth have a higher level of hydrogen in their breath at varying degrees depending on which ailment they carry.

Some embodiments provide a portable, hand-held breath analyzer including a main body and a removable mouthpiece, wherein the removable mouthpiece removably attaches to the main body. The main body includes a sensor, a processor, a power source and an electrical circuit. The electrical circuit operably connects the power source to the sensor and connects the sensor to the processor. The sensor comprises a hydrogen selective material and a conductive material, wherein the hydrogen selective material contacts the conductive material. The hydrogen selective material has a resistivity that increases in response to increased concentration of hydrogen. The processor detects resistivity of the sensor and uses the resistivity to calculate a concentration of hydrogen in a breath sample.

In some cases, the hydrogen selective material comprises polyaniline, wherein the polyaniline is doped with a dopant that increases pH sensitivity of the polyaniline, and wherein the polyaniline has a resistivity that increases in response to increased concentration of hydrogen. In certain cases, the polyaniline has a pH sensitivity of more than 59 mV. The dopant can include a protonic acid in some embodiments, such as a protonic acid selected from the group consisting of hydrochloric acid, sulfuric acid, salicylic acid, acetic acid, citric acid, tartaric acid, oxalic acid, malonic acid, succinic acid, glutamic acid, adipic acid, phthalic acid and camphor sulfonic acid. In certain cases, the dopant comprises hydrochloric acid.

In some cases, the conductive material comprises a plurality of electrodes. The plurality of electrodes can have any desired arrangement, such as a plurality of interdigitated finger electrodes. Also, in some cases, the hydrogen selective material is deposited as a thin film on the conductive material.

Some embodiments provide a breath test method for screening for a gastrointestinal disorder. The screening method includes providing a portable, hand-held breath analyzer, prompting a subject to exhale a breath sample into a removable mouthpiece, allowing the processor to measure a resistivity of a sensor that occurs when the breath sample contacts the sensor, and designating the subject as having an increased likelihood of having a gastrointestinal disorder if the measured resistivity is above and/or beneath a predetermined value. In some cases, the gastrointestinal disorder is celiac disease. In other cases, the gastrointestinal disorder is non-celiac gluten sensitivity.

Other embodiments provide a breath test method for diagnosing a gastrointestinal disorder. The diagnostic method includes providing a portable, hand-held breath analyzer, prompting a subject to exhale a breath sample into a removable mouthpiece, allowing the processor to measure a resistivity of a sensor that occurs when the breath sample contacts the sensor, and diagnosing the subject as having a gastrointestinal disorder if the measured resistivity is above and/or beneath a predetermined value. In some cases, the gastrointestinal disorder is celiac disease. In other cases, the gastrointestinal disorder is non-celiac gluten sensitivity.

Other embodiments provide a breath test method for screening for lactose intolerance. The screening method includes providing a portable, hand-held breath analyzer, prompting a subject to exhale a baseline breath sample into a removable mouthpiece, allowing the processor to measure a resistivity of a sensor that occurs when the baseline breath sample contacts the sensor, prompting a subject to ingest a lactose-containing meal, prompting a subject to exhale a post-lactose breath sample into the removable mouthpiece, allowing the processor to measure a resistivity of the sensor that occurs when the post-lactose breath sample contacts the sensor, comparing the measured resistivity of the baseline breath sample to the measured resistivity of the post-lactose breath sample, and designating the subject as having an increased likelihood of having lactose intolerance if the comparing meets a predetermined criteria. In some cases, the designating the subject as having an increased likelihood of having lactose intolerance occurs when the measured resistivity is above and/or beneath a predetermined value.

In some embodiments, the breath test method for screening for lactose intolerance includes prompting a subject to exhale a first post-lactose breath sample into the removable mouthpiece at a first time point, allowing the processor to measure a resistivity of the sensor that occurs when the first post-lactose breath sample contacts the sensor, prompting a subject to exhale a second post-lactose breath sample into the removable mouthpiece at a second time point, allowing the processor to measure a resistivity of the sensor that occurs when the second post-lactose breath sample contacts the sensor, comparing the measured resistivity of the baseline breath sample, the first post-lactose breath sample and the second post-lactose breath sample, and designating the subject as having an increased likelihood of having lactose intolerance if the comparing meets a predetermined criteria.

In other embodiments, the breath test method for screening for lactose intolerance includes prompting a subject to exhale a first post-lactose breath sample into the removable mouthpiece at a first time point, allowing the processor to measure a resistivity of the sensor that occurs when the first post-lactose breath sample contacts the sensor, prompting a subject to exhale a second post-lactose breath sample into the removable mouthpiece at a second time point, allowing the processor to measure a resistivity of the sensor that occurs when the second post-lactose breath sample contacts the sensor, prompting a subject to exhale a third post-lactose breath sample into the removable mouthpiece at a third time point, allowing the processor to measure a resistivity of the sensor that occurs when the third post-lactose breath sample contacts the sensor, prompting a subject to exhale a fourth post-lactose breath sample into the removable mouthpiece at a fourth time point, allowing the processor to measure a resistivity of the sensor that occurs when the fourth post-lactose breath sample contacts the sensor, comparing the measured resistivity of the baseline breath sample, the first post-lactose breath sample, the second post-lactose breath sample, the third post-lactose breath sample and the fourth post-lactose breath sample, and designating the subject as having an increased likelihood of having lactose intolerance if the comparing meets a predetermined criteria. In some cases, the first time point is a 30 minute time point, the second time point is a 60 minute time point, the third time point is a 90 minute time point and the fourth time point is a 120 minute time point.

Other embodiments provide a breath test method for diagnosing lactose intolerance. The screening method includes providing a portable, hand-held breath analyzer, prompting a subject to exhale a baseline breath sample into a removable mouthpiece, allowing the processor to measure a resistivity of a sensor that occurs when the baseline breath sample contacts the sensor, prompting a subject to ingest a lactose-containing meal, prompting a subject to exhale a post-lactose breath sample into the removable mouthpiece, allowing the processor to measure a resistivity of the sensor that occurs when the post-lactose breath sample contacts the sensor, comparing the measured resistivity of the baseline breath sample to the measured resistivity of the post-lactose breath sample, and diagnosing the subject with lactose intolerance if the comparing meets a predetermined criteria. In some cases, the diagnosing the subject with lactose intolerance occurs when the measured resistivity is above and/or beneath a predetermined value.

In some embodiments, the breath test method for diagnosing lactose intolerance includes prompting a subject to exhale a first post-lactose breath sample into the removable mouthpiece at a first time point, allowing the processor to measure a resistivity of the sensor that occurs when the first post-lactose breath sample contacts the sensor, prompting a subject to exhale a second post-lactose breath sample into the removable mouthpiece at a second time point, allowing the processor to measure a resistivity of the sensor that occurs when the second post-lactose breath sample contacts the sensor, comparing the measured resistivity of the baseline breath sample, the first post-lactose breath sample and the second post-lactose breath sample, and diagnosing the subject with lactose intolerance if the comparing meets a predetermined criteria.

In other embodiments, the breath test method for diagnosing lactose intolerance includes prompting a subject to exhale a first post-lactose breath sample into the removable mouthpiece at a first time point, allowing the processor to measure a resistivity of the sensor that occurs when the first post-lactose breath sample contacts the sensor, prompting a subject to exhale a second post-lactose breath sample into the removable mouthpiece at a second time point, allowing the processor to measure a resistivity of the sensor that occurs when the second post-lactose breath sample contacts the sensor, prompting a subject to exhale a third post-lactose breath sample into the removable mouthpiece at a third time point, allowing the processor to measure a resistivity of the sensor that occurs when the third post-lactose breath sample contacts the sensor, prompting a subject to exhale a fourth post-lactose breath sample into the removable mouthpiece at a fourth time point, allowing the processor to measure a resistivity of the sensor that occurs when the fourth post-lactose breath sample contacts the sensor, comparing the measured resistivity of the baseline breath sample, the first post-lactose breath sample, the second post-lactose breath sample, the third post-lactose breath sample and the fourth post-lactose breath sample; and diagnosing the subject with lactose intolerance if the comparing meets a predetermined criteria. In some cases, the first time point is a 30 minute time point, the second time point is a 60 minute time point, the third time point is a 90 minute time point and the fourth time point is a 120 minute time point.

Other embodiments provide a breath test method for screening for fructose intolerance. The screening method includes providing a portable, hand-held breath analyzer, prompting a subject to exhale a baseline breath sample into a removable mouthpiece, allowing the processor to measure a resistivity of a sensor that occurs when the baseline breath sample contacts the sensor, prompting a subject to ingest a fructose-containing meal, prompting a subject to exhale a post-fructose breath sample into the removable mouthpiece, allowing the processor to measure a resistivity of the sensor that occurs when the post-fructose breath sample contacts the sensor, comparing the measured resistivity of the baseline breath sample to the measured resistivity of the post-fructose breath sample, and designating the subject as having an increased likelihood of having fructose intolerance if the comparing meets a predetermined criteria. In some cases, the designating the subject as having an increased likelihood of having fructose intolerance occurs when the measured resistivity is above and/or beneath a predetermined value.

In some embodiments, the breath test method for screening for fructose intolerance includes prompting a subject to exhale a first post-fructose breath sample into the removable mouthpiece at a first time point, allowing the processor to measure a resistivity of the sensor that occurs when the first post-fructose breath sample contacts the sensor, prompting a subject to exhale a second post-fructose breath sample into the removable mouthpiece at a second time point, allowing the processor to measure a resistivity of the sensor that occurs when the second post-fructose breath sample contacts the sensor, comparing the measured resistivity of the baseline breath sample, the first post-fructose breath sample and the second post-fructose breath sample, and designating the subject as having an increased likelihood of having fructose intolerance if the comparing meets a predetermined criteria.

In other embodiments, the breath test method for screening for fructose intolerance includes prompting a subject to exhale a first post-fructose breath sample into the removable mouthpiece at a first time point, allowing the processor to measure a resistivity of the sensor that occurs when the first post-fructose breath sample contacts the sensor, prompting a subject to exhale a second post-fructose breath sample into the removable mouthpiece at a second time point, allowing the processor to measure a resistivity of the sensor that occurs when the second post-fructose breath sample contacts the sensor, prompting a subject to exhale a third post-fructose breath sample into the removable mouthpiece at a third time point, allowing the processor to measure a resistivity of the sensor that occurs when the third post-fructose breath sample contacts the sensor, prompting a subject to exhale a fourth post-fructose breath sample into the removable mouthpiece at a fourth time point, allowing the processor to measure a resistivity of the sensor that occurs when the fourth post-fructose breath sample contacts the sensor, comparing the measured resistivity of the baseline breath sample, the first post-fructose breath sample, the second post-fructose breath sample, the third post-fructose breath sample and the fourth post-fructose breath sample; and designating the subject as having an increased likelihood of having fructose intolerance if the comparing meets a predetermined criteria. In some cases, the first time point is a 30 minute time point, the second time point is a 60 minute time point, the third time point is a 90 minute time point and the fourth time point is a 120 minute time point.

Other embodiments provide a breath test method for diagnosing fructose intolerance. The screening method includes providing a portable, hand-held breath analyzer, prompting a subject to exhale a baseline breath sample into a removable mouthpiece, allowing the processor to measure a resistivity of a sensor that occurs when the baseline breath sample contacts the sensor, prompting a subject to ingest a fructose-containing meal, prompting a subject to exhale a post-fructose breath sample into the removable mouthpiece, allowing the processor to measure a resistivity of the sensor that occurs when the post-fructose breath sample contacts the sensor, comparing the measured resistivity of the baseline breath sample to the measured resistivity of the post-fructose breath sample, and diagnosing the subject with fructose intolerance if the comparing meets a predetermined criteria. In some cases, the diagnosing the subject with fructose intolerance occurs when the measured resistivity is above and/or beneath a predetermined value.

In some embodiments, the breath test method for diagnosing fructose intolerance includes prompting a subject to exhale a first post-fructose breath sample into the removable mouthpiece at a first time point, allowing the processor to measure a resistivity of the sensor that occurs when the first post-fructose breath sample contacts the sensor, prompting a subject to exhale a second post-fructose breath sample into the removable mouthpiece at a second time point, allowing the processor to measure a resistivity of the sensor that occurs when the second post-fructose breath sample contacts the sensor, comparing the measured resistivity of the baseline breath sample, the first post-fructose breath sample and the second post-fructose breath sample, and diagnosing the subject with fructose intolerance if the comparing meets a predetermined criteria.

In other embodiments, the breath test method for diagnosing fructose intolerance includes prompting a subject to exhale a first post-fructose breath sample into the removable mouthpiece at a first time point, allowing the processor to measure a resistivity of the sensor that occurs when the first post-fructose breath sample contacts the sensor, prompting a subject to exhale a second post-fructose breath sample into the removable mouthpiece at a second time point, allowing the processor to measure a resistivity of the sensor that occurs when the second post-fructose breath sample contacts the sensor, prompting a subject to exhale a third post-fructose breath sample into the removable mouthpiece at a third time point, allowing the processor to measure a resistivity of the sensor that occurs when the third post-fructose breath sample contacts the sensor, prompting a subject to exhale a fourth post-fructose breath sample into the removable mouthpiece at a fourth time point, allowing the processor to measure a resistivity of the sensor that occurs when the fourth post-fructose breath sample contacts the sensor, comparing the measured resistivity of the baseline breath sample, the first post-fructose breath sample, the second post-fructose breath sample, the third post-fructose breath sample and the fourth post-fructose breath sample; and diagnosing the subject with fructose intolerance if the comparing meets a predetermined criteria. In some cases, the first time point is a 30 minute time point, the second time point is a 60 minute time point, the third time point is a 90 minute time point and the fourth time point is a 120 minute time point.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives. For example, each time the term "comprising" is used, in alternative embodiments, "comprising" can be replaced with "consisting essentially of" or "consisting of."

The present invention provides an improved breath analyzer and breath test method to determine the presence of a gastrointestinal disorder (e.g., celiac disease, non-celiac gluten sensitivity, lactose intolerance, fructose intolerance or small bowel bacterial overgrowth) in a subject's digestive tract. The improved breath analyzer and breath test is less costly and more convenient than existing methods.

Figure 2:
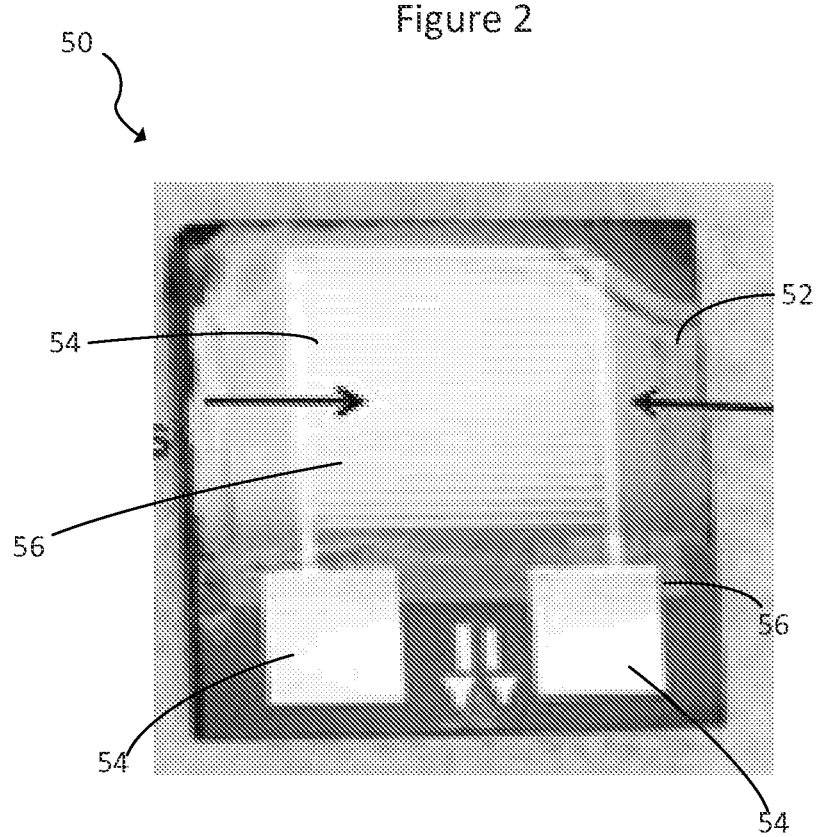
FIG. 2 shows an embodiment of a hydrogen sensor.

FIG. 2 illustrates an exemplary embodiment of a hydrogen detecting sensor 50. The hydrogen detecting sensor 50 includes a substrate 52, a conductive material 54 and hydrogen selective material 56. The conductive material 54 is provided on the substrate 52 and the hydrogen selective material 56 contacts the conductive material 54.

The conductive material 54 includes any desired conductive material. In some cases, the conductive material 54 is platinum. In other cases, the conductive material 54 is gold. In certain cases, the conductive material 54 is an electrode arrangement. The electrode arrangement can be a single electrode or a plurality of electrodes. The electrodes can be spaced apart in any desired arrangement. In some cases, the electrodes are spaced less than about 250 μm apart, perhaps less than about 150 μm apart, such as about 100 μm apart. In certain cases, the electrodes are spaced less than about 10 μm apart, such as 5 μm apart. In some cases, the electrodes include interdigitated finger electrodes. In one embodiment, the sensor comprises interdigitated platinum finger electrodes with a line spacing of 100 μm apart or less. In the embodiment of FIG. 2, the conductive material 54 is provided as an arrangement of interdigitated finger electrodes.

The hydrogen selective material 56 includes any material that has a resistivity that increases in response to increased presence of hydrogen. In some cases, the hydrogen selective material 56 is a hydrogen selective metal oxide. In certain cases, the hydrogen selective material 56 comprises a hydrogen selective zinc oxide. In other cases, the hydrogen selective material 56 comprises a hydrogen selective metal oxide film. In particular cases, the hydrogen selective material 56 comprises a hydrogen selective metal zinc oxide film. In other cases, the hydrogen selective material 56 comprises zinc oxide nanowires. In certain cases, the hydrogen selective material 56 comprises a film comprising zinc oxide nanowires. In some cases, the zinc oxide nanowires can have a diameter of 200 nm or less, such as 100 nm.

In some cases, the hydrogen selective material 56 includes doped polyaniline. Polyaniline exhibits three different oxidation states: leucoemeraldine (LEB, fully reduced), emeraldine (EB, half-oxidized), and pernigraniline (PNB, fully oxidized). Also, when polyaniline is in the emeraldine state, it can be in either an emeraldine salt or emeraldine base form. When in the emeraldine salt form, the polyaniline is conducting. The emeraldine salt form is usually obtained by protonating the basic amine and imine sites with strong acids. This process is reversible in that the emeraldine base form is obtained by deprotonating the amine groups. Thus, the emeraldine state of polyaniline transitions between an acid form and base form. FIG. 1 shows the acid-base transition of polyaniline.

The acid-base transition of polyaniline renders it pH sensitive and this characteristic allows it to be effectively used in hydrogen detection. When hydrogen contacts an emeraldine salt form of polyaniline, the hydrogen deprotonates the amine groups and converts it to an emeraldine base, which also causes an increase in resistivity and a corresponding decrease in conductivity.

Further, the polyaniline can be doped with a protonic acid to increase its pH sensitivity. A polyaniline with increased pH sensitivity is desirable for hydrogen detection because when hydrogen converts the polyaniline to an emeraldine base, it causes an even larger increase in resistivity and corresponding decrease in conductivity. Larger increases in resistivity (and decreases in conductivity) are desirable because they are easier to detect and increase the sensitivity of the polyaniline to hydrogen.

Polyaniline doped with a protonic acid has an increase in pH sensitivity compared to an undoped polyaniline. In some cases, the polyaniline can be doped with a protonic acid including ions such $Cl^-$ and $SO_4^2$ to obtain pH sensitivity of around 59 mV. Certain protonic acids cause for an even larger increase in pH sensitivity. For example, polyaniline doped with camphor sulfonic acid has been shown to have a pH sensitivity of around 70 mV.

In some cases, the polyaniline comprises at least one dopant that increases pH sensitivity of the polyaniline. In some cases, the dopant is a protonic acid. In some embodiments, the dopant is hydrochloric acid. In other embodiments, the dopant is camphor sulfonic acid. In yet other embodiments, the dopant is both hydrochloric acid and camphor sulfonic acid. Other possible dopants include sulfuric acid, salicylic acid, acetic acid, citric acid, tartaric acid, oxalic acid, malonic acid, succinic acid, glutamic acid, adipic acid and phthalic acid. Also, in some cases, the polyaniline has a dopant that provides the polyaniline with a pH sensitivity of more than 59 mV. In one embodiment, the polyaniline has a camphor sulfonic acid dopant, which provides the polyaniline with a pH sensitivity of about 70 mV, which is a higher sensitivity observed than when using other dopants.

Also, the hydrogen selective material 56 can be deposited directly onto the conductive material 52 using any desired deposition process. For example, the hydrogen selective material 56 can be deposited onto the conductive material 52 using a spin coating method, a chemical vapor deposition method or a sputtering method. In certain cases, the conductive material 52 is coated with spun cast hydrogen selective material 56. In certain embodiments, the hydrogen selective material 56 is doped polyaniline deposited directly onto the conductive material 52 using a spin coating method. The sensor 50 also includes contact pads 54. The sensor 50 is connected to an electrical circuit via contact pads 54.

The sensor 50 detects hydrogen at very low ppb levels. In some cases, the sensor 50 detects breath hydrogen at levels lower than 40 ppm (<40 ppm) and as high as 100 ppm, thereby covering all hydrogen levels encountered in humans. In certain cases, the sensor 50 detects breath hydrogen at levels lower than 40 ppm. In other cases, the sensor 50 detects breath hydrogen at levels between about 1 ppm and about 100 ppm.

Certain embodiments provide a breath analyzer that detects presence and concentration of hydrogen in a breath sample. The breath analyzer includes an input, a sensor, an electrical circuit and a processor. The input receives a breath sample. The sensor contacts the breath sample. The sensor can have any of the embodiments described herein. In some cases, the sensor includes hydrogen selective material (e.g., doped polyaniline) and a conductive material. The electrical circuit operable connects to the conductive material to the processor. The processor measures resistivity in the electrical circuit and uses the resistivity to calculate a concentration of hydrogen in the breath sample.

Figure 3:
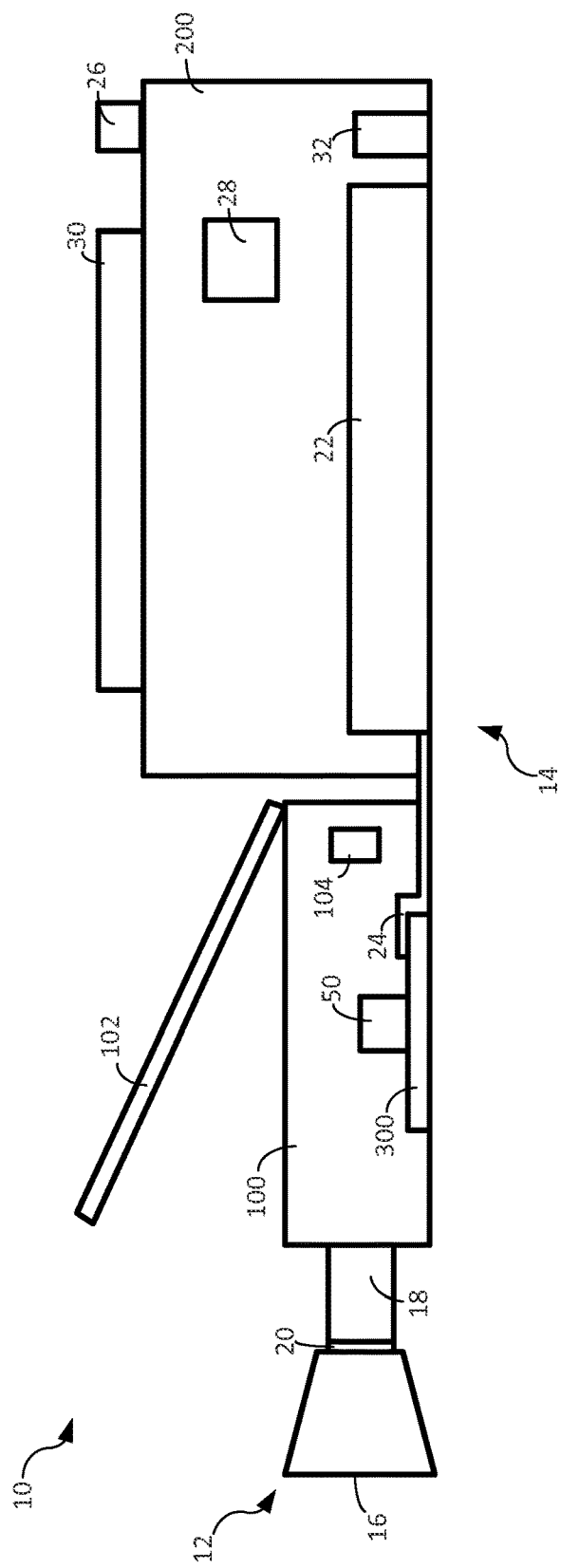
FIG. 3 shows a schematic of an embodiment of a breath analyzer.
Figure 5:
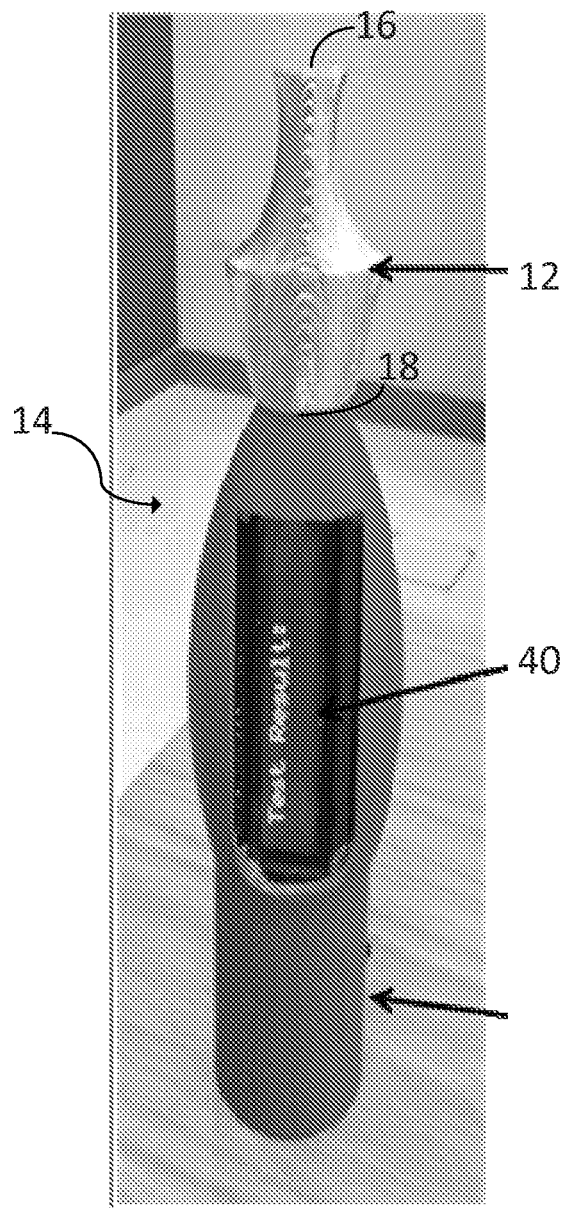
FIG. 5 shows an embodiment of a breath analyzer with a removable mouthpiece and a main body in an attached configuration.

FIG. 3 is a schematic of an exemplary embodiment of a breath analyzer 10. The breath analyzer 10 includes a removable mouthpiece 12 and a main body 14. FIGS. 4-5 also illustrate an exemplary design of the breath analyzer 10. FIG. 4 shows the breath analyzer 10 with a removable mouthpiece 12 and main body 14 in an attached configuration whereas FIG. 5 shows the breath analyzer 10 with the removable mouthpiece 12 attached to the main body 14. The breath analyzer 10 in these embodiments is provided as a self-contained, portable, hand-held device.

The removable mouthpiece 12 can include a first portion 16 and a second portion 18. The first portion 16 can be configured as an input that receives a breath sample. The first portion 16 can also be sized and shaped to receive a user's lips, so that a user can blow exhaled breath into the removable mouthpiece 12. The second portion 18 can be sized and shaped to removably connect to the main body 14. For example, the second portion 18 can be snapped onto or perhaps screwed onto the main body 14.

In some cases, the removable mouthpiece 12 further includes a one-way valve 20. In such cases, a user blows exhaled breath into the mouthpiece 12. The exhaled breath moves forward past the one-way valve 20 and becomes trapped. In other words, the exhaled breath cannot move backward past the one-way valve 20.

In certain embodiments, the mouthpiece 12 is a single-use mouthpiece. A single-use mouthpiece is desirable because it can be replaced for use with each new user. Also, in some cases, components of the mouthpiece 12 and/or main body 14 in contact with exhaled breath can be made of an inert or non-reactive material (e.g., polytetrafluoroethylene (PFTE)) that does not interfere with hydrogen absorption.

Figure 6:
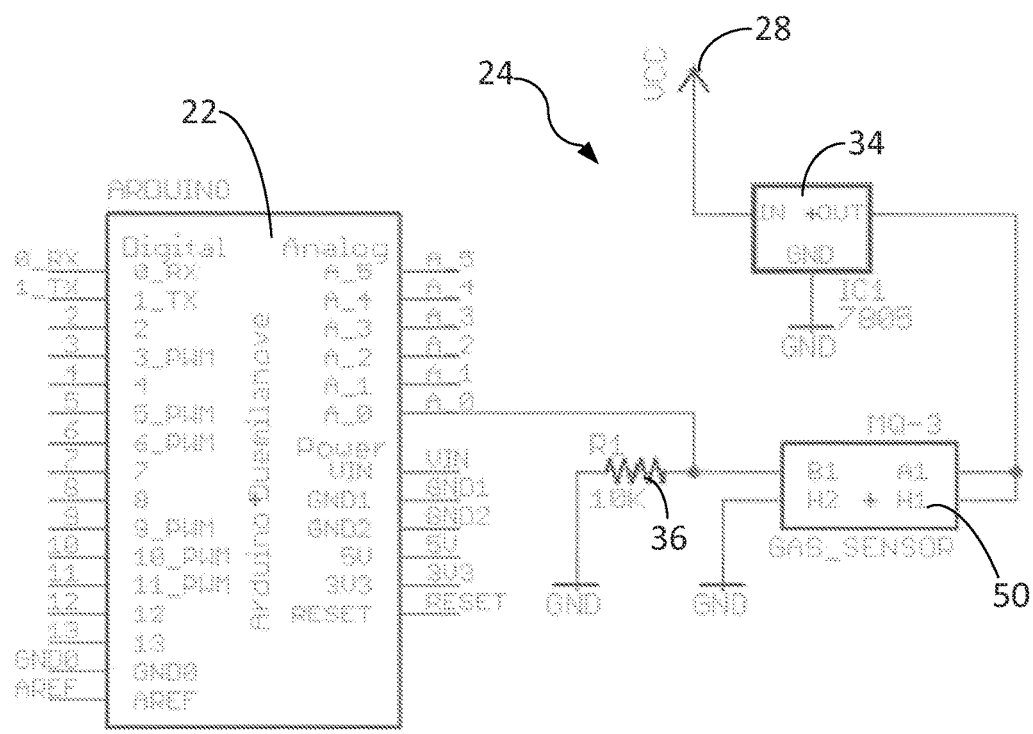
FIG. 6 shows an embodiment of an electrical schematic for the breath analyzer.

The main body 14 includes a sensor 50, a processor 22 and a power source 28. FIG. 6 is an electrical schematic illustrating the electrical connection between these components according to one embodiment. As shown, the sensor 50, processor 22 and power source 28 are electrically connected via an electrical circuit 24.

The processor 22 can be any desired processor known in the art. In some cases, the processor 22 is a microcontroller. In certain cases, the processor 22 is an Arduino microcontroller.

The sensor can have any of the embodiments already described. In some cases, the sensor includes the sensor 50 of the embodiment of FIG. 2. The sensor 50 is electrically connected to the electrical circuit using any desired connection mechanism. In some cases, the sensor 50 connects to the electrical circuit 24 via an optional sensor mount 300. In such cases, the sensor 50 can be mounted directly onto the sensor mount 300. The sensor mount 300 serves as an interface between the sensor 50 and the electrical circuit 24. Thus, the sensor mount 300 can be any structure known in the art that connects the electrodes 52 of the sensor 50 to the electrical circuit 24. In some embodiments, the sensor mount 300 is a printed circuit board.

In other cases, the sensor 50 is directly connected to the electrical circuit 24. For example, in some embodiments, the electrical circuit 24 includes two metal clips that can be clamped onto the contact pads 54 to create an electrical connection. A user can also replace an old sensor 50 with a new sensor by pulling the old sensor 50 out of the metal clips and inserting a new sensor 50 into the clips.

The main body 14 also includes an on/off button 26 and a power source 28. The power source 28 can be a portable power source, such as a battery. When the on/off button 26 is activated, the power source 28 turns on. As shown in FIG. 6, the power source 28 supplies voltage to a voltage regulator 24. In certain cases, the power source 28 supplies 9 volts to the voltage regulator 24. The voltage regulator 24 regulates the amount of voltage sent to the sensor 50. In some cases, the voltage regulator 24 supplies a voltage to the sensor 50 in the amount of between 0 volts to 5 volts. In certain cases, the voltage regulator 24 supplies a voltage to the sensor 50 in the amount of about 5 volts. In one embodiment, the voltage regulator 24 is an IC1 7805 voltage regulator, a product manufactured by Fairchild Electronics.

A resistor 36 is also electrically connected to the sensor 50 and provides resistance to the sensor. In some cases, the resistor 36 is a 10 kΩ resistor. When the breath sample contacts the sensor 50, a change in resistivity occurs in the sensor 50 that correlates to an amount of hydrogen in the sample. The sensor 50 outputs voltage (along with the changes in resistivity) to the processor 22. The processor 22 detects changes in resistivity and uses the changes in resistivity to calculate a concentration of hydrogen in the breath sample. The processor 22 can also compare a concentration of hydrogen between two different breath samples.

The main body 14 can also include a display 30 operably connected to the processor 22. In some cases, the display 30 shows the concentration of hydrogen calculated by the processor 22. In other cases, the display 30 shows results of a comparison between concentrations of hydrogen between two or more different breath samples. In some cases, the comparison results can show a positive comparison result or a negative comparison result that is determined using a predetermined positive/negative threshold. In other cases, the comparison results can show a numerical value that is the delta between a baseline hydrogen value and a post-substrate ingestion hydrogen value. The main body 14 can also include an optional wireless connector 32 (e.g., a Bluetooth connector) that transmits data calculated by the processor 22 to an external computer.

In some embodiments, the main body 14 is configured as including a first compartment 100 and a second compartment 200. In some cases, as shown in FIG. 3, the first compartment 100 is a chamber that houses a sensor 50 and sensor mount 300 and the second compartment 200 is an electrical housing that houses various components.

In some cases, the chamber 100 includes a lid or door 102 that opens and shuts. When the door 102 is closed, the chamber 100 provides a closed, sealed environment around the sensor 50. When the door 102 is open, the sensor 50 is accessible through the door opening. A user can open the chamber door 102 to remove and replace the sensor 50 as needed. The chamber 100 also includes an outlet 104. The outlet 104 includes a cap that can be opened to release a breath sample from the chamber 100 and closed to trap a breath sample within the chamber 100.

The removable mouthpiece 12 is connected to the chamber 100 such that exhaled breath passes from the mouthpiece 12 directly into the chamber 100. The breath analyzer 10 can include an optional desiccant assembly 60. The desiccant assembly 60 helps to remove excess moisture from the exhaled breath. In some embodiments, the desiccant assembly 60 is provided inside of the mouthpiece 12. In other embodiments, the desiccant assembly 60 is provided inside of the chamber 100. Exhaled breath first moves through the desiccant assembly 60 before coming into contact with the sensor 50.

Figure 7:
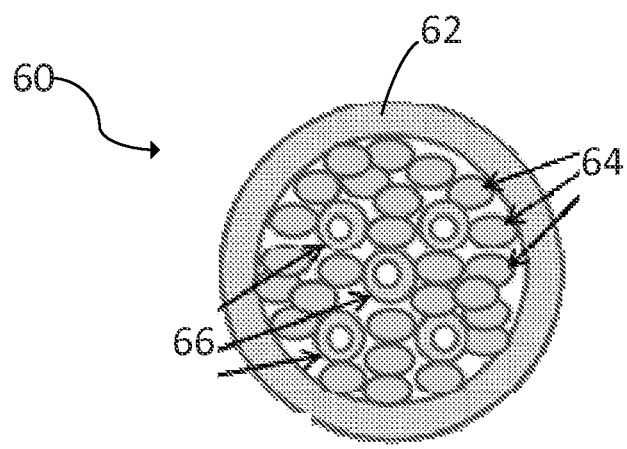
FIG. 7 shows an embodiment of a desiccant assembly.

FIG. 7 shows an exemplary embodiment of a desiccant assembly 60. In some cases, the desiccant assembly is provided as a tube 62 upon which exhaled air flows through.

Figure 8:
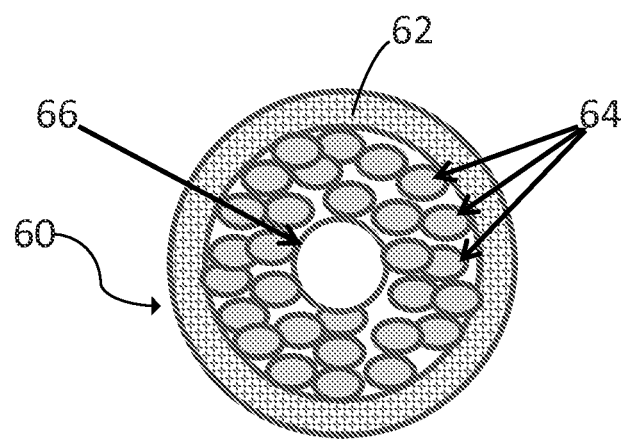
FIG. 8 shows another embodiment of a desiccant assembly.

The tube 62 can have an interior filled with a plurality of desiccant beads 64. The desiccant beads 64 can also be arranged such that a plurality of channels 66 are created for exhaled air to flow through. FIG. 8 shows another exemplary embodiment of a desiccant assembly 60. In this embodiment, the tube can have an interior filled with a plurality of desiccant beads 64 arranged such that a single channel 66 is created.

Still further, the breath analyzer 10 can include an optional gas filter (not shown). The gas filter helps to remove a selected gas (e.g., carbon dioxide, nitrogen, ammonia and/or hydrogen) from the exhaled breath. In some embodiments, the gas filter is provided inside of the mouthpiece 12. In other embodiments, the gas filter is provided inside of the chamber 100. Exhaled breath first moves through the gas filter before coming into contact with the sensor 50.

Referring back to FIG. 3, the main body 14 can also include a second compartment configured as an electrical housing 200 that houses various components. In the illustrate embodiment, the electrical housing 200 houses the processor 22, parts of the electrical circuit 24, a power source 28, a display 30, and a wireless connector 32.

During use, a user turns the breath analyzer 10 on by activating the on/off switch 26. The on/off switch 26 can be located anywhere about an exterior surface of the main body 14. This on/off switch 26 in turn prompts the power source 28 to supply voltage to the voltage regulator 34. The voltage regulator 34 regulates and supplies voltage to the sensor 50. The resistor 36 also supplies resistance to the sensor 50.

A user then blows a breath sample into the first portion 16 of the mouthpiece 12. The breath sample moves past the one way valve 20 and through the optional desiccant/gas filter 60. The breath sample then moves out of the optional desiccant/gas filter 60 and into the chamber 100 where it contacts the sensor 50. The breath sample causes a change in resistivity to occur in the sensor 50. This resistivity is outputted to the processor 22.

Other embodiments provide a breath test method for screening for a gastrointestinal disorder. Some embodiments provide a breath test method for screening for celiac disease. In some cases, the screening method includes steps of: collecting a fasting breath sample from a subject, exposing the fasting breath sample to a sensor comprising hydrogen selective material having a resistivity that increases in response to increased presence of hydrogen, measuring resistivity the sensor that occurs when the fasting breath sample contacts the sensor and designating the subject as having an increased likelihood of having a celiac disease if the measured resistivity is above and/or beneath a predetermined value. The fasting breath sample can include a single sample from a subject after fasting. In some cases, the fasting breath sample is a sample from a subject after fasting for at least 2 hours, 3 hours, 4 hours, 5 hours, 6 hours, 7 hours or 8 hours.

In some cases, the breath test screening method for celiac disease is performed in connection with a breath analyzer. The breath analyzer can have any of the embodiments described herein. In some cases, the breath analyzer includes a portable, hand-held breath analyzer. The breath test screening method includes steps of: providing a breath analyzer having a sensor comprising hydrogen selective material having a resistivity that increases in response to increased presence of hydrogen, prompting a subject to exhale a fasting breath sample into the breath analyzer, allowing the breath analyzer to measure a resistivity of the sensor, and designating the subject as having an increased likelihood of having celiac disease if the measured resistivity is above and/or beneath a predetermined value.

In some cases, the breath analyzer includes a main body and a removable mouthpiece, wherein the removable mouthpiece removably attaches to the main body, wherein the main body includes a sensor, a processor, a power source and an electrical circuit, wherein the electrical circuit operably connects the power source to the sensor and connects the sensor to the processor, wherein the sensor comprises a conductive material and hydrogen selective material in contact with the conductive material, wherein the hydrogen selective material has a resistivity that increases in response to increased concentration of hydrogen. The breath test screening method includes steps of: turning on a breath analyzer by activating an on/off switch, prompting a subject to exhale a fasting breath sample into the removable mouthpiece, allowing the processor to measure a resistivity of the sensor that occurs when the fasting breath sample contacts the sensor, and designating the subject as having an increased likelihood of having celiac disease if the measured resistivity is above and/or beneath a predetermined value.

Other embodiments provide a breath test method for diagnosing a subject with celiac disease. The breath test diagnostic method includes steps of: collecting a fasting breath sample from a subject, exposing the fasting breath sample to a sensor comprising hydrogen selective material having a resistivity that increases in response to increased presence of hydrogen, measuring resistivity of the fasting breath sample and diagnosing the subject with celiac disease if the measured resistivity is above and/or beneath a predetermined value.

In some cases, the breath test diagnostic method for celiac disease is performed in connection with a breath analyzer. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a fasting breath sample into the breath analyzer, allowing the breath analyzer to measure a resistivity of the sensor, and diagnosing the subject with celiac disease if the measured resistivity is above and/or beneath a predetermined value.

In some cases, the breath analyzer includes a main body and a removable mouthpiece, wherein the removable mouthpiece removably attaches to the main body, wherein the main body includes a sensor, a processor, a power source and an electrical circuit, wherein the electrical circuit operably connects the power source to the sensor and connects the sensor to the processor, wherein the sensor comprises a conductive material and hydrogen selective material in contact with the conductive material, wherein the hydrogen selective material has a resistivity that increases in response to increased concentration of hydrogen. The breath test screening method includes steps of: turning on a breath analyzer by activating an on/off switch, prompting the subject to exhale a fasting breath sample into the removable mouthpiece, allowing the processor to measure a resistivity of the sensor that occurs when the fasting breath sample contacts the sensor, and diagnosing the subject with celiac disease if the measured resistivity is above and/or beneath a predetermined value.

Some embodiments provide a breath test method for screening for NCGS. In some cases, the screening method includes steps of: collecting a fasting breath sample from a subject, exposing the fasting breath sample to a sensor comprising hydrogen selective material having a resistivity that increases in response to increased presence of hydrogen, measuring resistivity of the sensor that occurs when the fasting breath sample contacts the sensor and designating the subject as having an increased likelihood of having a NCGS if the measured resistivity is above and/or beneath a predetermined value. The fasting breath sample can include a single sample from a subject after fasting. In some cases, the fasting breath sample is a sample from a subject after fasting for at least 2 hours, 3 hours, 4 hours, 5 hours, 6 hours, 7 hours or 8 hours.

In some cases, the breath test screening method is performed in connection with a breath analyzer. The breath analyzer can have any of the embodiments described herein. In some cases, the breath analyzer includes a portable, hand-held breath analyzer. The breath test screening method includes steps of: providing a breath analyzer having a sensor comprising hydrogen selective material having a resistivity that increases in response to increased presence of hydrogen, prompting a subject to exhale a fasting breath sample into the breath analyzer, allowing the breath analyzer to measure a resistivity of the sensor, and designating the subject as having an increased likelihood of having NCGS if the measured resistivity is above and/or beneath a predetermined value.

In some cases, the breath analyzer includes a main body and a removable mouthpiece, wherein the removable mouthpiece removably attaches to the main body, wherein the main body includes a sensor, a processor, a power source and an electrical circuit, wherein the electrical circuit operably connects the power source to the sensor and connects the sensor to the processor, wherein the sensor comprises a conductive material and hydrogen selective material in contact with the conductive material, wherein the hydrogen selective material has a resistivity that increases in response to increased concentration of hydrogen. The breath test screening method includes steps of: turning on a breath analyzer by activating an on/off switch, prompting a subject to exhale a fasting breath sample into the removable mouthpiece, allowing the processor to measure a resistivity of the sensor that occurs when the fasting breath sample contacts the sensor, and designating the subject as having an increased likelihood of having NCGS if the measured resistivity is above and/or beneath a predetermined value.

Other embodiments provide a breath test method for diagnosing a subject with NCGS. The breath test diagnostic method includes steps of: collecting a fasting breath sample from a subject, exposing the fasting breath sample to a sensor comprising hydrogen selective material having a resistivity that increases in response to increased presence of hydrogen, measuring resistivity of the fasting breath sample and diagnosing the subject with NCGS if the measured resistivity is above and/or beneath a predetermined value.

In some cases, the breath test diagnostic method for NCGS is performed in connection with a breath analyzer. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a fasting breath sample into the breath analyzer, allowing the breath analyzer to measure a resistivity of the sensor, and diagnosing the subject with NCGS if the measured resistivity is above and/or beneath a predetermined value.

In some cases, the breath analyzer includes a main body and a removable mouthpiece, wherein the removable mouthpiece removably attaches to the main body, wherein the main body includes a sensor, a processor, a power source and an electrical circuit, wherein the electrical circuit operably connects the power source to the sensor and connects the sensor to the processor, wherein the sensor comprises a conductive material and hydrogen selective material in contact with the conductive material, wherein the hydrogen selective material has a resistivity that increases in response to increased concentration of hydrogen. The breath test screening method includes steps of: turning on a breath analyzer by activating an on/off switch, prompting the subject to exhale a fasting breath sample into the removable mouthpiece, allowing the processor to measure a resistivity of the sensor that occurs when the fasting breath sample contacts the sensor, and diagnosing the subject with NCGS if the measured resistivity is above and/or beneath a predetermined value.

Other embodiments provide a breath test method for screening for lactose intolerance. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-lactose breath sample from a subject, exposing the post-lactose breath sample to a sensor comprising hydrogen selective material having a resistivity that increases in response to increased presence of hydrogen, measuring resistivity of the post-lactose breath sample, comparing the measured resistivity of the baseline breath sample and the post-lactose breath sample and designating the subject has having an increased likelihood of having lactose intolerance when comparing meets a predetermined criteria. The baseline breath sample can obtained after fasting for a time period and before ingesting the lactose-containing material. The post-lactose breath sample can include a sample from the same subject after ingesting a lactose-containing meal. The post-lactose breath sample can be obtained at a time period after ingesting the lactose-containing material. For example, the post-lactose breath sample can obtained at a time period of 20-30 minutes after ingesting the lactose-containing material. In some cases, the post-lactose breath sample is obtained at a time period of 30 minutes after ingesting the lactose-containing material.

In some embodiments, the step of collecting a post-lactose breath sample comprises collecting post-lactose breath samples at a plurality different time points. For example, in some cases, the plurality of time points include at least a first time point and a second time point. In other cases, the plurality of time points include at least a first time point, a second time point, a third time point and a fourth time point. In other cases, the plurality of time points include at least a first time point, a second time point, a third time point, a fourth time point and a fifth time point. In yet other cases, the plurality of time points include at least a first time point, a second time point, a third time point, a fourth time point, a fifth time point and a sixth time point. The time points can be spaced at any desired interval, such as a 15 minute interval, a 20 minute interval or a 30 minute interval. In certain cases, the first time point is a 15 minute time point, the second time point is a 30 minute time point, the third time point is a 45 minute time point, the fourth time point is a 60 minute time point, the fifth time point is a 75 minute time point and the sixth time point is a 90 minute time point. In other cases, the first time point is a 30 minute time point, the second time point is a 60 minute time point, the third time point is a 90 minute time point, the fourth time point is a 120 minute time point, the fifth time point is a 150 minute time point and the sixth time point is a 180 minute time point. Likewise, any desired number of time points can be used and the time points can be spaced by any desired time interval.

In some cases, the screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-lactose breath sample from a subject at a first time point, exposing the first post-lactose breath sample to a sensor comprising hydrogen selective material having a resistivity that increases in response to increased presence of hydrogen, measuring resistivity of the first post-lactose breath sample, collecting a second post-lactose breath sample from a subject at a second time point, exposing the second post-lactose breath sample to a sensor comprising hydrogen selective material having a resistivity that increases in response to increased presence of hydrogen, measuring resistivity of the second post-lactose breath sample, comparing the resistivity of the baseline breath sample, first post-lactose breath sample and second post-lactose breath sample and designating the subject has having an increased likelihood of having lactose intolerance when the comparing meets a predetermined criteria.

In some cases, the step of collecting a post-lactose breath sample comprises collecting a plurality of post-lactose breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a lactose-containing meal, collecting a first post-lactose breath sample from a subject at a first time point, exposing the first post-lactose breath sample to the sensor, measuring a resistivity of the sensor that occurs when the first post-lactose breath sample contacts the sensor, collecting a second post-lactose breath sample from a subject at a second time point, exposing the second post-lactose breath sample to the sensor, measuring a resistivity of the sensor that occurs when the second post-lactose breath sample contacts the sensor, collecting a third post-lactose breath sample from a subject at a third time point, exposing the third post-lactose breath sample to the sensor, measuring a resistivity of the sensor that occurs when the third post-lactose breath sample contacts the sensor, collecting a fourth post-lactose breath sample from a subject at a second time point, exposing the fourth post-lactose breath sample to the sensor, measuring a resistivity of the sensor that occurs when the fourth post-lactose breath sample contacts the sensor, comparing the resistivity of the baseline breath sample, the first post-lactose breath sample, the second post-lactose breath sample, the third post-lactose breath sample and the fourth post-lactose breath sample and designating the subject has having an increased likelihood of having lactose intolerance when the comparing meets a predetermined criteria.

In some cases, the breath test screening method for screening for lactose intolerance is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-lactose breath sample into the breath analyzer, allowing the breath analyzer to measure a resistivity of the sensor that occurs when the post-lactose ingestion breath sample contacts the sensor, comparing the measured resistivity of the baseline breath sample to the measured resistivity of the post-lactose breath sample and designating the subject as having an increased likelihood of having lactose intolerance when the comparing meets a predetermined criteria.

In other cases, the breath test screening method includes steps of: providing a breath analyzer having a sensor comprising hydrogen selective material having a resistivity that increases in response to increased presence of hydrogen, prompting a subject to exhale a baseline breath sample into the breath analyzer for a time period, allowing the breath analyzer to measure a resistivity of the sensor that occurs with the baseline breath sample, resetting the breath analyzer, prompting a subject to exhale a first post-lactose breath sample into the breath analyzer, allowing the breath analyzer to measure a resistivity of the sensor that occurs with the first post-lactose ingestion breath sample, resetting the breath analyzer, prompting a subject to exhale a second post-lactose breath sample into the breath analyzer, allowing the breath analyzer to measure a resistivity of the sensor that occurs with the second post-lactose ingestion breath sample, comparing the measured resistivity of the baseline breath sample, the first post-lactose breath sample and the second post-lactose breath sample, and designating the subject as having an increased likelihood of having lactose intolerance when the comparing meets a predetermined criteria.

In other cases, the breath test method for screening for lactose intolerance includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-lactose breath sample into the breath analyzer, allowing the breath analyzer to measure a resistivity of the sensor that occurs with the first post-lactose ingestion breath sample, resetting the breath analyzer, prompting a subject to exhale a second post-lactose breath sample into the breath analyzer, allowing the breath analyzer to measure a resistivity of the sensor that occurs with the second post-lactose ingestion breath sample, resetting the breath analyzer, prompting a subject to exhale a third post-lactose breath sample into the breath analyzer, allowing the breath analyzer to measure a resistivity of the sensor that occurs with the third post-lactose ingestion breath sample, resetting the breath analyzer, prompting a subject to exhale a fourth post-lactose breath sample into the breath analyzer, allowing the breath analyzer to measure a resistivity of the sensor that occurs with the fourth post-lactose ingestion breath sample, comparing the measured resistivity of the baseline breath sample, the first post-lactose breath sample, the second post-lactose breath sample, the third post-lactose breath sample and the fourth post-lactose breath sample, and designating the subject as having an increased likelihood of having lactose intolerance when the comparing meets a predetermined criteria.

Other embodiments provide a breath test method for diagnosing lactose intolerance. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-lactose breath sample from a subject, exposing the post-lactose breath sample to a sensor comprising hydrogen selective material having a resistivity that increases in response to increased presence of hydrogen, measuring resistivity of the post-lactose breath sample, comparing the measured resistivity of the baseline breath sample and the post-lactose breath sample and diagnosing the subject with lactose intolerance when the comparing meets a predetermined criteria.

In some cases, the step of collecting a post-lactose breath sample comprises collecting a plurality of post-lactose breath samples at different time points. In such cases, the diagnostic method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-lactose breath sample from a subject at a first time point, exposing the first post-lactose breath sample to a sensor comprising hydrogen selective material having a resistivity that increases in response to increased presence of hydrogen, measuring resistivity of the first post-lactose breath sample, collecting a second post-lactose breath sample from a subject at a second time point, exposing the second post-lactose breath sample to a sensor comprising hydrogen selective material having a resistivity that increases in response to increased presence of hydrogen, measuring resistivity of the second post-lactose breath sample, comparing the resistivity of the baseline breath sample, first post-lactose breath sample and second post-lactose breath sample and diagnosing the subject with lactose intolerance when the comparing meets a predetermined criteria.

In some cases, the step of collecting a post-lactose breath sample comprises collecting a plurality of post-lactose breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a lactose-containing meal, collecting a first post-lactose breath sample from a subject at a first time point, exposing the first post-lactose breath sample to the sensor, measuring a resistivity of the sensor that occurs when the first post-lactose breath sample contacts the sensor, collecting a second post-lactose breath sample from a subject at a second time point, exposing the second post-lactose breath sample to the sensor, measuring a resistivity of the sensor that occurs when the second post-lactose breath sample contacts the sensor, collecting a third post-lactose breath sample from a subject at a third time point, exposing the third post-lactose breath sample to the sensor, measuring a resistivity of the sensor that occurs when the third post-lactose breath sample contacts the sensor, collecting a fourth post-lactose breath sample from a subject at a second time point, exposing the fourth post-lactose breath sample to the sensor, measuring a resistivity of the sensor that occurs when the fourth post-lactose breath sample contacts the sensor, comparing the resistivity of the baseline breath sample, the first post-lactose breath sample, the second post-lactose breath sample, the third post-lactose breath sample and the fourth post-lactose breath sample and diagnosing the subject with lactose intolerance when the comparing meets a predetermined criteria.

In some cases, the breath test diagnostic method is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-lactose breath sample into the breath analyzer, allowing the breath analyzer to measure a resistivity of the sensor that occurs when the post-lactose ingestion breath sample contacts the sensor, comparing the measured resistivity of the baseline breath sample to the measured resistivity of the post-lactose breath sample and diagnosing the subject with lactose intolerance when the comparing meets a predetermined criteria.

In other cases, the breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-lactose breath sample into the breath analyzer, allowing the breath analyzer to measure a resistivity of the sensor that occurs with the first post-lactose ingestion breath sample, resetting the breath analyzer, prompting a subject to exhale a second post-lactose breath sample into the breath analyzer, allowing the breath analyzer to measure a resistivity of the sensor that occurs with the second post-lactose ingestion breath sample, comparing the measured resistivity of the baseline breath sample, the first post-lactose breath sample and the second post-lactose breath sample, and diagnosing the subject with lactose intolerance when the comparing meets a predetermined criteria.

In other cases, the breath test diagnostic method includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-lactose breath sample into the breath analyzer, allowing the breath analyzer to measure a resistivity of the sensor that occurs with the first post-lactose ingestion breath sample, resetting the breath analyzer, prompting a subject to exhale a second post-lactose breath sample into the breath analyzer, allowing the breath analyzer to measure a resistivity of the sensor that occurs with the second post-lactose ingestion breath sample, resetting the breath analyzer, prompting a subject to exhale a third post-lactose breath sample into the breath analyzer, allowing the breath analyzer to measure a resistivity of the sensor that occurs with the third post-lactose ingestion breath sample, resetting the breath analyzer, prompting a subject to exhale a fourth post-lactose breath sample into the breath analyzer, allowing the breath analyzer to measure a resistivity of the sensor that occurs with the fourth post-lactose ingestion breath sample, comparing the measured resistivity of the baseline breath sample, the first post-lactose breath sample, the second post-lactose breath sample, the third post-lactose breath sample and the fourth post-lactose breath sample, and diagnosing the subject with lactose intolerance when the comparing meets a predetermined criteria.

Other embodiments provide a breath test method for screening for fructose intolerance. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-fructose breath sample from a subject, exposing the post-fructose breath sample to a sensor comprising hydrogen selective material having a resistivity that increases in response to increased presence of hydrogen, measuring resistivity of the post-fructose breath sample, comparing the measured resistivity of the baseline breath sample and the post-fructose breath sample and designating the subject has having an increased likelihood of having fructose intolerance when comparing meets a predetermined criteria. The baseline breath sample can obtained after fasting for a time period and before ingesting the fructose-containing material. The post-fructose breath sample can include a sample from the same subject after ingesting a fructose-containing meal. The post-fructose breath sample can be obtained at a time period after ingesting the fructose-containing material. In some cases, the post-fructose breath sample is obtained at a time period of 20-30 minutes after ingesting the fructose-containing material. In other cases, the post-fructose breath sample is obtained at a time period of 30 minutes after ingesting the fructose-containing material.

In some embodiments, the step of collecting a post-fructose breath sample comprises collecting post-fructose breath samples at a plurality different time points. For example, in some cases, the plurality of time points include at least a first time point and a second time point. In other cases, the plurality of time points include at least a first time point, a second time point, a third time point and a fourth time point. In other cases, the plurality of time points include at least a first time point, a second time point, a third time point, a fourth time point and a fifth time point. In yet other cases, the plurality of time points include at least a first time point, a second time point, a third time point, a fourth time point, a fifth time point and a sixth time point. The time points can be spaced at any desired interval, such as a 15 minute interval, a 20 minute interval or a 30 minute interval. In certain cases, the first time point is a 15 minute time point, the second time point is a 30 minute time point, the third time point is a 45 minute time point, the fourth time point is a 60 minute time point, the fifth time point is a 75 minute time point and the sixth time point is a 90 minute time point. In other cases, the first time point is a 30 minute time point, the second time point is a 60 minute time point, the third time point is a 90 minute time point, the fourth time point is a 120 minute time point, the fifth time point is a 150 minute time point and the sixth time point is a 180 minute time point. Likewise, any desired number of time points can be used and the time points can be spaced by any desired time interval.

In some cases, the screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-fructose breath sample from a subject at a first time point, exposing the first post-fructose breath sample to a sensor comprising hydrogen selective material having a resistivity that increases in response to increased presence of hydrogen, measuring resistivity of the first post-fructose breath sample, collecting a second post-fructose breath sample from a subject at a second time point, exposing the second post-fructose breath sample to a sensor comprising hydrogen selective material having a resistivity that increases in response to increased presence of hydrogen, measuring resistivity of the second post-fructose breath sample, comparing the resistivity of the baseline breath sample, first post-fructose breath sample and second post-fructose breath sample and designating the subject has having an increased likelihood of having fructose intolerance when the comparing meets a predetermined criteria.

In some cases, the step of collecting a post-fructose breath sample comprises collecting a plurality of post-fructose breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a fructose-containing meal, collecting a first post-fructose breath sample from a subject at a first time point, exposing the first post-fructose breath sample to the sensor, measuring a resistivity of the sensor that occurs when the first post-fructose breath sample contacts the sensor, collecting a second post-fructose breath sample from a subject at a second time point, exposing the second post-fructose breath sample to the sensor, measuring a resistivity of the sensor that occurs when the second post-fructose breath sample contacts the sensor, collecting a third post-fructose breath sample from a subject at a third time point, exposing the third post-fructose breath sample to the sensor, measuring a resistivity of the sensor that occurs when the third post-fructose breath sample contacts the sensor, collecting a fourth post-fructose breath sample from a subject at a second time point, exposing the fourth post-fructose breath sample to the sensor, measuring a resistivity of the sensor that occurs when the fourth post-fructose breath sample contacts the sensor, comparing the resistivity of the baseline breath sample, the first post-fructose breath sample, the second post-fructose breath sample, the third post-fructose breath sample and the fourth post-fructose breath sample and designating the subject has having an increased likelihood of having fructose intolerance when the comparing meets a predetermined criteria.

In some cases, the breath test screening method for screening for fructose intolerance is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-fructose breath sample into the breath analyzer, allowing the breath analyzer to measure a resistivity of the sensor that occurs when the post-fructose ingestion breath sample contacts the sensor, comparing the measured resistivity of the baseline breath sample to the measured resistivity of the post-fructose breath sample and designating the subject as having an increased likelihood of having fructose intolerance when the comparing meets a predetermined criteria.

In other cases, the breath test screening method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-fructose breath sample into the breath analyzer, allowing the breath analyzer to measure a resistivity of the sensor that occurs with the first post-fructose ingestion breath sample, resetting the breath analyzer, prompting a subject to exhale a second post-fructose breath sample into the breath analyzer, allowing the breath analyzer to measure a resistivity of the sensor that occurs with the second post-fructose ingestion breath sample, comparing the measured resistivity of the baseline breath sample, the first post-fructose breath sample and the second post-fructose breath sample, and designating the subject as having an increased likelihood of having fructose intolerance when the comparing meets a predetermined criteria.

In other cases, the breath test method for screening for fructose intolerance includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-fructose breath sample into the breath analyzer, allowing the breath analyzer to measure a resistivity of the sensor that occurs with the first post-fructose ingestion breath sample, resetting the breath analyzer, prompting a subject to exhale a second post-fructose breath sample into the breath analyzer, allowing the breath analyzer to measure a resistivity of the sensor that occurs with the second post-fructose ingestion breath sample, resetting the breath analyzer, prompting a subject to exhale a third post-fructose breath sample into the breath analyzer, allowing the breath analyzer to measure a resistivity of the sensor that occurs with the third post-fructose ingestion breath sample, resetting the breath analyzer, prompting a subject to exhale a fourth post-fructose breath sample into the breath analyzer, allowing the breath analyzer to measure a resistivity of the sensor that occurs with the fourth post-fructose ingestion breath sample, comparing the measured resistivity of the baseline breath sample, the first post-fructose breath sample, the second post-fructose breath sample, the third post-fructose breath sample and the fourth post-fructose breath sample, and designating the subject as having an increased likelihood of having fructose intolerance when the comparing meets a predetermined criteria.

Other embodiments provide a breath test method for diagnosing fructose intolerance. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-fructose breath sample from a subject, exposing the post-fructose breath sample to a sensor comprising hydrogen selective material having a resistivity that increases in response to increased presence of hydrogen, measuring resistivity of the post-fructose breath sample, comparing the measured resistivity of the baseline breath sample and the post-fructose breath sample and diagnosing the subject with fructose intolerance when the comparing meets a predetermined criteria.

In some cases, the step of collecting a post-fructose breath sample comprises collecting a plurality of post-fructose breath samples at different time points. In such cases, the diagnostic method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-fructose breath sample from a subject at a first time point, exposing the first post-fructose breath sample to a sensor comprising hydrogen selective material having a resistivity that increases in response to increased presence of hydrogen, measuring resistivity of the first post-fructose breath sample, collecting a second post-fructose breath sample from a subject at a second time point, exposing the second post-fructose breath sample to a sensor comprising hydrogen selective material having a resistivity that increases in response to increased presence of hydrogen, measuring resistivity of the second post-fructose breath sample, comparing the resistivity of the baseline breath sample, first post-fructose breath sample and second post-fructose breath sample and diagnosing the subject with fructose intolerance when the comparing meets a predetermined criteria.

In some cases, the step of collecting a post-fructose breath sample comprises collecting a plurality of post-fructose breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a fructose-containing meal, collecting a first post-fructose breath sample from a subject at a first time point, exposing the first post-fructose breath sample to the sensor, measuring a resistivity of the sensor that occurs when the first post-fructose breath sample contacts the sensor, collecting a second post-fructose breath sample from a subject at a second time point, exposing the second post-fructose breath sample to the sensor, measuring a resistivity of the sensor that occurs when the second post-fructose breath sample contacts the sensor, collecting a third post-fructose breath sample from a subject at a third time point, exposing the third post-fructose breath sample to the sensor, measuring a resistivity of the sensor that occurs when the third post-fructose breath sample contacts the sensor, collecting a fourth post-fructose breath sample from a subject at a second time point, exposing the fourth post-fructose breath sample to the sensor, measuring a resistivity of the sensor that occurs when the fourth post-fructose breath sample contacts the sensor, comparing the resistivity of the baseline breath sample, the first post-fructose breath sample, the second post-fructose breath sample, the third post-fructose breath sample and the fourth post-fructose breath sample and diagnosing the subject with fructose intolerance when the comparing meets a predetermined criteria.

In some cases, the breath test diagnostic method is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-fructose breath sample into the breath analyzer, allowing the breath analyzer to measure a resistivity of the sensor that occurs when the post-fructose ingestion breath sample contacts the sensor, comparing the measured resistivity of the baseline breath sample to the measured resistivity of the post-fructose breath sample and diagnosing the subject with fructose intolerance when the comparing meets a predetermined criteria.

In other cases, the breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-fructose breath sample into the breath analyzer, allowing the breath analyzer to measure a resistivity of the sensor that occurs with the first post-fructose ingestion breath sample, resetting the breath analyzer, prompting a subject to exhale a second post-fructose breath sample into the breath analyzer, allowing the breath analyzer to measure a resistivity of the sensor that occurs with the second post-fructose ingestion breath sample, comparing the measured resistivity of the baseline breath sample, the first post-fructose breath sample and the second post-fructose breath sample, and diagnosing the subject with fructose intolerance when the comparing meets a predetermined criteria.

In other cases, the breath test diagnostic method includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-fructose breath sample into the breath analyzer, allowing the breath analyzer to measure a resistivity of the sensor that occurs with the first post-fructose ingestion breath sample, resetting the breath analyzer, prompting a subject to exhale a second post-fructose breath sample into the breath analyzer, allowing the breath analyzer to measure a resistivity of the sensor that occurs with the second post-fructose ingestion breath sample, resetting the breath analyzer, prompting a subject to exhale a third post-fructose breath sample into the breath analyzer, allowing the breath analyzer to measure a resistivity of the sensor that occurs with the third post-fructose ingestion breath sample, resetting the breath analyzer, prompting a subject to exhale a fourth post-fructose breath sample into the breath analyzer, allowing the breath analyzer to measure a resistivity of the sensor that occurs with the fourth post-fructose ingestion breath sample, comparing the measured resistivity of the baseline breath sample, the first post-fructose breath sample, the second post-fructose breath sample, the third post-fructose breath sample and the fourth post-fructose breath sample, and diagnosing the subject with fructose intolerance when the comparing meets a predetermined criteria.

Other embodiments provide a breath test method for screening for SIBO. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-substrate breath sample from a subject, exposing the post-substrate breath sample to a sensor comprising hydrogen selective material having a resistivity that increases in response to increased presence of hydrogen, measuring resistivity of the post-substrate breath sample, comparing the measured resistivity of the baseline breath sample and the post-substrate breath sample and designating the subject has having an increased likelihood of having SIBO when comparing meets a predetermined criteria. The baseline breath sample can obtained after fasting for a time period and before ingesting the substrate. In some cases, the substrate can be a glucose-containing meal. In other cases, the substrate can be a lactulose-containing meal. The post-substrate breath sample can include a sample from the same subject after ingesting a substrate. The post-substrate breath sample can be obtained at a time period after ingesting the substrate. In some cases, the post-substrate breath sample is obtained at a time period of 20-30 minutes after ingesting the substrate. In other cases, the post-substrate breath sample is obtained at a time period of 30 minutes after ingesting the substrate.

In some embodiments, the step of collecting a post-substrate breath sample comprises collecting post-substrate breath samples at a plurality different time points. For example, in some cases, the plurality of time points include at least a first time point and a second time point. In other cases, the plurality of time points include at least a first time point, a second time point, a third time point and a fourth time point. In other cases, the plurality of time points include at least a first time point, a second time point, a third time point, a fourth time point and a fifth time point. In yet other cases, the plurality of time points include at least a first time point, a second time point, a third time point, a fourth time point, a fifth time point and a sixth time point. The time points can be spaced at any desired interval, such as a 15 minute interval, a 20 minute interval or a 30 minute interval. In certain cases, the first time point is a 15 minute time point, the second time point is a 30 minute time point, the third time point is a 45 minute time point, the fourth time point is a 60 minute time point, the fifth time point is a 75 minute time point and the sixth time point is a 90 minute time point. In other cases, the first time point is a 30 minute time point, the second time point is a 60 minute time point, the third time point is a 90 minute time point, the fourth time point is a 120 minute time point, the fifth time point is a 150 minute time point and the sixth time point is a 180 minute time point. Likewise, any desired number of time points can be used and the time points can be spaced by any desired time interval.

In some cases, the screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-substrate breath sample from a subject at a first time point, exposing the first post-substrate breath sample to a sensor comprising hydrogen selective material having a resistivity that increases in response to increased presence of hydrogen, measuring resistivity of the first post-substrate breath sample, collecting a second post-substrate breath sample from a subject at a second time point, exposing the second post-substrate breath sample to a sensor comprising hydrogen selective material having a resistivity that increases in response to increased presence of hydrogen, measuring resistivity of the second post-substrate breath sample, comparing the resistivity of the baseline breath sample, first post-substrate breath sample and second post-substrate breath sample and designating the subject has having an increased likelihood of having SIBO when the comparing meets a predetermined criteria.

In some cases, the step of collecting a post-substrate breath sample comprises collecting a plurality of post-substrate breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a substrate, collecting a first post-substrate breath sample from a subject at a first time point, exposing the first post-substrate breath sample to the sensor, measuring a resistivity of the sensor that occurs when the first post-substrate breath sample contacts the sensor, collecting a second post-substrate breath sample from a subject at a second time point, exposing the second post-substrate breath sample to the sensor, measuring a resistivity of the sensor that occurs when the second post-substrate breath sample contacts the sensor, collecting a third post-substrate breath sample from a subject at a third time point, exposing the third post-substrate breath sample to the sensor, measuring a resistivity of the sensor that occurs when the third post-substrate breath sample contacts the sensor, collecting a fourth post-substrate breath sample from a subject at a second time point, exposing the fourth post-substrate breath sample to the sensor, measuring a resistivity of the sensor that occurs when the fourth post-substrate breath sample contacts the sensor, comparing the resistivity of the baseline breath sample, the first post-substrate breath sample, the second post-substrate breath sample, the third post-substrate breath sample and the fourth post-substrate breath sample and designating the subject has having an increased likelihood of having SIBO when the comparing meets a predetermined criteria.

In some cases, the breath test screening method for screening for SIBO is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-substrate breath sample into the breath analyzer, allowing the breath analyzer to measure a resistivity of the sensor that occurs when the post-substrate ingestion breath sample contacts the sensor, comparing the measured resistivity of the baseline breath sample to the measured resistivity of the post-substrate breath sample and designating the subject as having an increased likelihood of having SIBO when the comparing meets a predetermined criteria.

In other cases, the breath test screening method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-substrate breath sample into the breath analyzer, allowing the breath analyzer to measure a resistivity of the sensor that occurs with the first post-substrate ingestion breath sample, resetting the breath analyzer, prompting a subject to exhale a second post-substrate breath sample into the breath analyzer, allowing the breath analyzer to measure a resistivity of the sensor that occurs with the second post-substrate ingestion breath sample, comparing the measured resistivity of the baseline breath sample, the first post-substrate breath sample and the second post-substrate breath sample, and designating the subject as having an increased likelihood of having SIBO when the comparing meets a predetermined criteria.

In other cases, the breath test method for screening for SIBO includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-substrate breath sample into the breath analyzer, allowing the breath analyzer to measure a resistivity of the sensor that occurs with the first post-substrate ingestion breath sample, resetting the breath analyzer, prompting a subject to exhale a second post-substrate breath sample into the breath analyzer, allowing the breath analyzer to measure a resistivity of the sensor that occurs with the second post-substrate ingestion breath sample, resetting the breath analyzer, prompting a subject to exhale a third post-substrate breath sample into the breath analyzer, allowing the breath analyzer to measure a resistivity of the sensor that occurs with the third post-substrate ingestion breath sample, resetting the breath analyzer, prompting a subject to exhale a fourth post-substrate breath sample into the breath analyzer, allowing the breath analyzer to measure a resistivity of the sensor that occurs with the fourth post-substrate ingestion breath sample, comparing the measured resistivity of the baseline breath sample, the first post-substrate breath sample, the second post-substrate breath sample, the third post-substrate breath sample and the fourth post-substrate breath sample, and designating the subject as having an increased likelihood of having SIBO when the comparing meets a predetermined criteria.

Other embodiments provide a breath test method for diagnosing SIBO. The breath test screening method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a post-substrate breath sample from a subject, exposing the post-substrate breath sample to a sensor comprising hydrogen selective material having a resistivity that increases in response to increased presence of hydrogen, measuring resistivity of the post-substrate breath sample, comparing the measured resistivity of the baseline breath sample and the post-substrate breath sample and diagnosing the subject with SIBO when the comparing meets a predetermined criteria.

In some cases, the step of collecting a post-substrate breath sample comprises collecting a plurality of post-substrate breath samples at different time points. In such cases, the diagnostic method includes steps of: collecting a baseline breath sample from a subject, exposing the baseline breath sample to a sensor comprising hydrogen selective material having a resistivity that increases in response to increased presence of hydrogen, measuring resistivity of the baseline breath sample, collecting a first post-substrate breath sample from a subject at a first time point, exposing the first post-substrate breath sample to a sensor comprising hydrogen selective material having a resistivity that increases in response to increased presence of hydrogen, measuring resistivity of the first post-substrate breath sample, collecting a second post-substrate breath sample from a subject at a second time point, exposing the second post-substrate breath sample to a sensor comprising hydrogen selective material having a resistivity that increases in response to increased presence of hydrogen, measuring resistivity of the second post-substrate breath sample, comparing the resistivity of the baseline breath sample, first post-substrate breath sample and second post-substrate breath sample and diagnosing the subject with SIBO when the comparing meets a predetermined criteria.

In some cases, the step of collecting a post-substrate breath sample comprises collecting a plurality of post-substrate breath samples at four time points. In such cases, the screening method includes steps of: collecting a baseline breath sample from a subject, exposing the baseline breath sample to a sensor comprising hydrogen selective material having a resistivity that increases in response to increased presence of hydrogen, measuring a resistivity of the sensor that occurs when the baseline breath sample contacts the sensor, prompting the subject to ingest a substrate-containing meal, collecting a first post-substrate breath sample from a subject at a first time point, exposing the first post-substrate breath sample to the sensor, measuring a resistivity of the sensor that occurs when the first post-substrate breath sample contacts the sensor, collecting a second post-substrate breath sample from a subject at a second time point, exposing the second post-substrate breath sample to the sensor, measuring a resistivity of the sensor that occurs when the second post-substrate breath sample contacts the sensor, collecting a third post-substrate breath sample from a subject at a third time point, exposing the third post-substrate breath sample to the sensor, measuring a resistivity of the sensor that occurs when the third post-substrate breath sample contacts the sensor, collecting a fourth post-substrate breath sample from a subject at a second time point, exposing the fourth post-substrate breath sample to the sensor, measuring a resistivity of the sensor that occurs when the fourth post-substrate breath sample contacts the sensor, comparing the resistivity of the baseline breath sample, the first post-substrate breath sample, the second post-substrate breath sample, the third post-substrate breath sample and the fourth post-substrate breath sample and diagnosing the subject with SIBO when the comparing meets a predetermined criteria.

In some cases, the breath test diagnostic method is performed in connection with a breath analyzer. The breath analyzer can have any of the embodiments described herein. In some cases, the breath analyzer includes a portable, hand-held breath analyzer. The breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs when the baseline breath sample contacts the sensor, resetting the breath analyzer, prompting a subject to exhale a post-substrate breath sample into the breath analyzer, allowing the breath analyzer to measure a resistivity of the sensor that occurs when the post-substrate breath sample contacts the sensor, comparing the measured resistivity of the baseline breath sample to the measured resistivity of the post-substrate breath sample and diagnosing the subject with SIBO when the comparing meets a predetermined criteria.

In other cases, the breath test diagnostic method includes steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-substrate breath sample into the breath analyzer, allowing the breath analyzer to measure a resistivity of the sensor that occurs with the first post-substrate breath sample, resetting the breath analyzer, prompting a subject to exhale a second post-substrate breath sample into the breath analyzer, allowing the breath analyzer to measure a resistivity of the sensor that occurs with the second post-substrate breath sample, comparing the measured resistivity of the baseline breath sample, the first post-substrate breath sample and the second post-substrate breath sample, and diagnosing the subject with SIBO when the comparing meets a predetermined criteria.

In other cases, the breath test diagnostic method includes the steps of: providing a breath analyzer having a sensor comprising hydrogen selective material having a resistivity that increases in response to increased presence of hydrogen, prompting a subject to exhale a baseline breath sample into the breath analyzer, allowing the breath analyzer to measure a resistivity of the sensor that occurs with the baseline breath sample, resetting the breath analyzer, prompting a subject to exhale a first post-substrate breath sample into the breath analyzer, allowing the breath analyzer to measure a resistivity of the sensor that occurs with the first post-substrate breath sample, resetting the breath analyzer, prompting a subject to exhale a second post-substrate breath sample into the breath analyzer, allowing the breath analyzer to measure a resistivity of the sensor that occurs with the second post-substrate breath sample, resetting the breath analyzer, prompting a subject to exhale a third post-substrate breath sample into the breath analyzer, allowing the breath analyzer to measure a resistivity of the sensor that occurs with the third post-substrate breath sample, resetting the breath analyzer, prompting a subject to exhale a fourth post-substrate breath sample into the breath analyzer, allowing the breath analyzer to measure a resistivity of the sensor that occurs with the fourth post-substrate breath sample, comparing the measured resistivity of the baseline breath sample, the first post-substrate breath sample, the second post-substrate breath sample, the third post-substrate breath sample and the fourth post-substrate breath sample, and diagnosing the subject with SIBO when the comparing meets a predetermined criteria.

In each of the above breath test methods, the baseline breath sample is a sample from a subject after fasting for at least 2 hours, 3 hours, 4 hours, 5 hours, 6 hours, 7 hours or 8 hours. In some cases, the baseline breath sample is a sample from a subject after fasting for at least 8 hours. Also, the step of resetting the breath analyzer comprises flushing the sensor with atmospheric air. In certain cases, the step of flushing the sensor with atmospheric air comprises opening an outlet in the sensor to release the breath sample, allowing the sensor to return to a baseline resistivity and closing the outlet. In other embodiments, the step of resetting the breath analyzer comprises replacing the sensor. In some cases, the step of replacing the sensor occurs each time a breath sample is measured.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A handheld, portable breath analyzer, comprising:
   a main body;
   a removable mouthpiece, wherein the removable mouthpiece removably attaches to the main body; and
   a gas filter, the gas filter being located in either the removable mouthpiece or the main body;
   wherein the main body includes a sensor, a processor, a power source and an electrical circuit;
   wherein the electrical circuit operably connects the power source to the sensor and connects the sensor to the processor;
   wherein the sensor comprises a conductive material and a hydrogen selective material in contact with the conductive material, wherein the hydrogen selective material has a resistivity that increases in response to increased concentration of hydrogen, wherein the hydrogen selective material comprises polyaniline, wherein the polyaniline is doped with a dopant that increases pH sensitivity of the polyaniline, and wherein the polyaniline has a resistivity that increases in response to increased concentration of hydrogen;
   wherein the gas filter is configured to remove ammonia from a breath sample exhaled into the removable mouthpiece, and wherein the breath sample is configured to move through the gas filter before coming into contact with the sensor; and
   wherein the processor detects resistivity of the sensor and uses the resistivity to calculate a concentration of hydrogen.

2. The breath analyzer of claim 1 wherein the polyaniline has a pH sensitivity of more than 59 mV.

3. The breath analyzer of claim 1 wherein the dopant comprises a protonic acid.

4. The breath analyzer of claim 3 wherein the dopant comprises a protonic acid selected from the group consisting of hydrochloric acid, sulfuric acid, salicylic acid, acetic acid, citric acid, tartaric acid, oxalic acid, malonic acid, succinic acid, glutamic acid, adipic acid, phthalic acid and camphor sulfonic acid.

5. The breath analyzer of claim 4 wherein the dopant consists essentially of hydrochloric acid.

6. The breath analyzer of claim 1 wherein the conductive material comprises a plurality of electrodes.

7. The breath analyzer of claim 6 wherein the plurality of electrodes are interdigitated finger electrodes.

8. The breath analyzer of claim 1 wherein the hydrogen selective material is deposited as a thin film on the conductive material.

9. The breath analyzer of claim 1 further comprising a desiccant, wherein the desiccant is located in either the removable mouthpiece or the main body.

10. The breath analyzer of claim 6 wherein the electrodes are spaced less than 10 μm apart.

11. The breath analyzer of claim 1 wherein the conductive material is gold.

12. The breath analyzer of claim 1 wherein the sensor detects hydrogen at levels between 1 ppm and 100 ppm.

13. The breath analyzer of claim 1 wherein the removable mouthpiece includes a one-way valve.

14. The breath analyzer of claim 1 wherein the conductive material is platinum.

15. A breath test method for screening for a gastrointestinal disorder, comprising steps of:
   (a) providing a portable, hand-held breath analyzer, wherein the portable, hand-held breath analyzer comprises:
      (i) a main body; and
      (ii) a removable mouthpiece, wherein the removable mouthpiece removably attaches to the main body,
      wherein the main body includes a sensor, a processor, a power source and an electrical circuit, wherein the electrical circuit operably connects the power source to the sensor and connects the sensor to the processor, wherein the sensor comprises a conductive material and a hydrogen selective material in contact with the conductive material, wherein the hydrogen selective material has a resistivity that increases in response to increased concentration of hydrogen, wherein the hydrogen selective material comprises polyaniline, wherein the polyaniline is doped with a dopant that increases pH sensitivity of the polyaniline, and wherein the polyaniline has a resistivity that increases in response to increased concentration of hydrogen, wherein the portable, hand-held breath analyzer further comprises a gas filter, the gas filter being located in either the removable mouthpiece or the main body;
   (b) prompting a subject to exhale a fasting breath sample into the removable mouthpiece;
   (c) allowing the processor to measure a resistivity of the sensor that occurs when the fasting breath sample contacts the sensor, the gas filter being configured to remove ammonia from the fasting breath sample before the fasting breath sample comes into contact with the sensor; and
   (d) designating the subject as having an increased likelihood of having a gastrointestinal disorder if the measured resistivity is above and/or beneath a predetermined value.

16. The breath test method of claim 15 wherein the gastrointestinal disorder is celiac disease.

17. The breath test method of claim 15 wherein the gastrointestinal disorder is non-celiac gluten sensitivity.

18. A breath test method for diagnosing a gastrointestinal disorder, comprising steps of:
(a) providing a portable, hand-held breath analyzer, wherein the portable, hand-held breath analyzer comprises:
(i) a main body; and
(ii) a removable mouthpiece, wherein the removable mouthpiece removably attaches to the main body, wherein the main body includes a sensor, a processor, a power source and an electrical circuit, wherein the electrical circuit operably connects the power source to the sensor and connects the sensor to the processor, wherein the sensor comprises a conductive material and a hydrogen selective material in contact with the conductive material, wherein the hydrogen selective material has a resistivity that increases in response to increased concentration of hydrogen, wherein the hydrogen selective material comprises polyaniline, wherein the polyaniline is doped with a dopant that increases pH sensitivity of the polyaniline, and wherein the polyaniline has a resistivity that increases in response to increased concentration of hydrogen, wherein the portable, hand-held breath analyzer further comprises a gas filter, the gas filter being located in either the removable mouthpiece or the main body;
(b) prompting a subject to exhale a fasting breath sample into the removable mouthpiece;
(c) allowing the processor to measure a resistivity of the sensor that occurs when the fasting breath sample contacts the sensor, the gas filter being configured to remove ammonia from the fasting breath sample before the fasting breath sample comes into contact with the sensor; and
(d) diagnosing the subject as having a gastrointestinal disorder if the measured resistivity is above and/or beneath a predetermined value.

19. The breath test method of claim 18 wherein the gastrointestinal disorder is celiac disease.

20. The breath test method of claim 18 wherein the gastrointestinal disorder is non-celiac gluten sensitivity.

* * * * *